United States Patent [19]
Beall et al.

[11] Patent Number: 5,760,308
[45] Date of Patent: Jun. 2, 1998

[54] METHOD AND APPARATUS FOR NON-DESTRUCTIVELY DETECTING HIDDEN DEFECTS CAUSED BY BIO-DETERIORATION IN LIVING TREES AND ROUND WOOD MATERIALS

[75] Inventors: Frank Carroll Beall, El Sobrante, Calif.; Richard Len Lemaster, Apex, N.C.; Jacek Marek Biernacki, Albany, Calif.

[73] Assignee: The Regents of the University of California, Oakland, Calif.

[21] Appl. No.: 843,553

[22] Filed: Apr. 18, 1997

Related U.S. Application Data

[60] Continuation of Ser. No. 457,810, Jun. 1, 1995, abandoned, which is a division of Ser. No. 301,811, Sep. 7, 1994.

[51] Int. Cl.$^6$ .................. G01N 29/08; G01N 29/18
[52] U.S. Cl. .................................... 73/644; 73/598
[58] Field of Search ........................ 73/644, 597, 598, 73/599, 600, 622, 632, 618

[56] References Cited

U.S. PATENT DOCUMENTS

| | | | |
|---|---|---|---|
| 3,600,937 | 8/1971 | Nilberg | 73/598 |
| 3,602,036 | 8/1971 | Peterson | 73/644 |
| 3,981,184 | 9/1976 | Matay | 73/622 |
| 4,386,527 | 6/1983 | Maucher | 73/597 |
| 5,097,881 | 3/1992 | Mack | 73/622 |

OTHER PUBLICATIONS

Miller, B.D., et al., A Sonic Method for Detecting Decay in Wood Poles, *Sixty-First Annual Meeting of the American Wood-Preservers' Association*, Apr. 26, 27 and 28, 1965, vol. 61, pp. 109–115.

McCracken, et al., "Sound Can Detect decay in Standing Hardwood Trees", *Research Paper SO–195*, United States Department of Agriculture, Forest Service, New Orleans, Louisiana, Aug. 1983, pp. 1–6.

Dunlop, J.I., "Testing of Poles by Using Acoustic Pulse Method", *Wood Sci. Technol.*, 15:301–310 (1981).

Vary, A., "The Acousto–Ultrasonic Approach", *Technical Memorandum NASA TM–89843*, Lewis Research Center, Cleveland, Ohio, pp. 1–21, Apr. 1987.

Kiernan, M.T., et al., "PC Analysis of an Acousto–Ultrasonic Signal", *Materials Evaluation*, 46, pp. 1344–1352, Sep. 1988.

(List continued on next page.)

*Primary Examiner*—Hezron E. Williams
*Assistant Examiner*—Nashmiya Fayyaz
*Attorney, Agent, or Firm*—Allston L. Jones

[57] ABSTRACT

A method and apparatus for detecting internal biodeterioration in round wood used in various applications (e.g. utility poles, pier pilings, round wood beams, posts and poles in structures, and living trees). The method includes the steps of securing a pulsing transducer adjacent one point on the surface of the round wood and securing a receiving transducer substantially diametrically opposite to the pulsing transducer. The pulsing transducer transmits ultrasonic signals through the round wood, which propagate through possibly deteriorated areas within the round wood. The receiving transducer receives the propagating ultrasonic signals, and a plurality of acousto-ultrasonic parameters contained in the received ultrasonic signals are processed and analyzed. The processing step includes the step of storing the averaged signals, and processing the stored signals on a real time basis to determine the acousto-ultrasonic parameters in the time and frequency domains. Optionally, the averaged signals are windowed and then stored before the AU parameters are processed and analyzed. The processing step further includes the step of generating at least one fixed frequency to cause the pulsing transducer to resonate and to inject ultrasonic signals at fixed frequencies. The pulsing and receiving transducers are secured to the round wood with a variety of coupling apparatus.

14 Claims, 16 Drawing Sheets

OTHER PUBLICATIONS

Wilcox, W., "Detection of early stages of wood decay with ultrasonic pulse velocity", *Forest Products Journal*, vol. 38, No. 5, pp. 68–73, May 1988.

Lemaster, Richard, et al., "The Use of Acousto–Ultrasonics to Detect Advance Decay in Round Wood", *Nondestructive Evaluation Center*, Forest Products Laboratory, University of California, Berkeley, Report No. 35.02.01, Nov. 1989.

Patton–Mallory, Marcia, P., et al., "Detecting Brown–rot Decay in Southern Yellow Pine by Acousto–Ultrasonics", *Seventh Symposium on the Nondestructive Testing of Wood Proceedings*, Sep. 27–29, 1989, pp. 29–44.

Beall, F.C., et al., "Wood: Acoustic Emission and Acousto–Ultrasonic Characteristics", *Concise Encyclopedia of Materials Characteristics*, R.W. Cahn and Eric Lifshin, Eds. Pergammon Press, pp. 551–554, (1993).

Davis, J., et al., "A Field Transportable Computerized Tomography Scanner for the Nondestructive Testing of Wooden Power Poles", *Materials Evaluation*, pp. 332–337, Mar. 1993.

Lemaster, Richard, et al., "The Use of Acousto–Ultrasonics to Detect Decay in Wood–Based Products", *Tropical Conference Proceedings Book, Second International Conference on Acousto–Ultrasonics*, Atlanta, Georgia, Jun. 24–25, 1993, pp. 181–190.

Beall, Frank, C., "Overview of Acousto–Ultrasonics Applied to Wood and Wood–Based Materials", *Topical Conference Proceedings Book, Second International Conference on Acousto–Ultrasonics*, Atlanta, Georgia, Jun. 24–25, 1993, pp. 153–161.

Lemaster, Richard, L, et al., "The feasibility of using acousto–ultrasonics to detect decay in utility poles", *Ninth International Symposium on Nondestructive Testing of Wood*, Sep. 22–24, 1993, Madison, Wisconsin, pp. 84–91.

METHOD AND APPARATUS FOR NON-DESTRUCTIVELY DETECTING HIDDEN DEFECTS CAUSED BY BIO-DETERIORATION IN LIVING TREES AND ROUND WOOD MATERIALS

This is a continuation of application of Ser. No. 08/457,810 filed on Jun. 1, 1995 and now abandoned, which was a divisional of copending application Ser. No. 08/301,811, still pending, filed on Sep. 7, 1994.

FIELD OF THE INVENTION

The present invention relates in general to ultrasonics, and more particularly it relates to a method and apparatus for using acousto-ultrasonics (AU) to perform non-intrusive detection of hidden defects caused by bio-deterioration in living trees and round wood poles and columns.

BACKGROUND OF THE INVENTION

Bio-deterioration of living trees, logs and round wood materials has long been of interest for various reasons from scientific investigation of the causes and effects to ways of slowing or preventing that deterioration. Much has been done to preserve round wood materials for various applications, however, even the best preservative techniques have not been able to truly preserve the round wood material in many of the applications for such materials. One commercial area where bio-deterioration of wooden poles has long been of interest is utility poles, and considerable research has been done in an effort to find a convenient, non-destructive technique or device for testing utility poles for deterioration with the pole in place.

Wooden utility poles are used extensively in the United States for the distribution of power and communications. Although utility poles are periodically replaced, a significantly high portion of these poles still have a useful service life, but are nonetheless often removed as a precautionary measure. If bio-deterioration is detected, it can often be arrested through treatment, thus prolonging the life of a pole. Because of preservative treatments, the removed poles are now classified as hazardous waste, substantially increasing disposal problems.

Beyond the direct cost savings of a reliable nondestructive evaluation (NDE) technique, the reduction of risk to line workers is an even greater benefit. Although a number of pole inspection techniques have been studied and developed, no field technique has gained wide acceptance by the utility companies. Many of these techniques lack sufficient sensitivity to detect all but advanced decay, are too expensive, or are too large or complex to make field inspections practical.

The two major forms of bio-deterioration in utility poles, as well as living trees and other wood products, are decay and insect attack. Most decay in utility poles occurs at or below the ground line and nearly always in areas opened up by checks or other damage to the poles. Checking is a grain separation in the longitudinal-radial plane, usually visible on the surface. The radial direction is from the surface toward the "biological center" of a pole. These checks are a normal event, caused by stresses developed during the drying of a pole; quite often, a large check provides sufficient stress relief to prevent further checking in other areas. Although utility poles are treated with preservatives to reduce bio-deterioration, the typical western softwoods used as poles often can be treated only in the sapwood, leaving the internal heartwood susceptible to deterioration.

The pattern of decay varies with species, but follows a sequential processes of incipient, intermediate, and advanced decay. Incipient decay normally occurs with little visible change of the wood, although the dynamic strength properties can be greatly reduced. The other extreme, advanced decay, is characterized by wood with no intrinsic strength. In order for fungal attack to occur, certain favorable conditions are needed, including "free water". In order to define the term "free water" it is first necessary to define the term "bound water". "Bound water" refers water retained by wood having a maximum moisture content of 25 to 30% (that level of water content is known as the "fiber saturation point"). "Free water" is then the moisture content of wood where the "fiber saturation point" has been exceeded. Each of these is determined on an oven dry mass basis for most wood species with free water being present in the lumens, or cell cavities, that make up about two-thirds of the volume of softwoods.

In California, three major types of termites cause damage to poles and other wood products, as well as living trees. The most damaging to utility poles are subterranean termites, which nest in the soil and attack the pole for food, usually through the embedded portion of the pole. In contrast, dry wood termites swarm through the air and will quite often enter the pole through some upper part, including the top. The third major type is wetwood termites, which are usually associated with destruction of downed trees in the forest. However, these termites will attack poles, particularly in portions that are wet. It is not uncommon to find both termite and fungal deterioration in poles.

The most widely-used pole inspection method consists of listening to the response from hammer impacts and then drilling or coring when appropriate. This "sounding" technique is accomplished by striking the pole around its periphery, from ground line to as high as can be reached. The characteristics of the sound of each impact are evaluated subjectively by the inspector, with a dull or hollow sound being considered indicative of deterioration. For suspect areas, the pole is drilled or cored to determine the extent of degradation. The cores are inspected for obvious defects and the holes are probed to determine the amount of shell or sound wood remaining. Accuracy of the technique depends on the skill of the inspector and can be reduced by the presence of conditions, other than deterioration, which can alter the sound, including high soil moisture content near the ground line, grain discontinuities, heavy concentrated loads, and the degree of pole restraint. Despite the crudeness of the technique, it is still the primary inspection method for many companies.

Considerable work has been conducted in an attempt to develop a reliable means of detecting decay in structural wood components. These methods can generally be classified as radiographical, electrical, mechanical, and acoustical. Early radiographic methods used conventional X-ray film as the detecting medium for a general profile of the pole. This progressed to electronic-type detectors and more recently to portable, computer-aided tomographic (CAT) scanners. All of these techniques produce images that are dependent on differences in density and composition of matter. Although advanced deterioration, especially voids, can be detected with these methods, the presence of moisture has often masked defects.

An electrically-based technique for the detection of decay uses the resistance to pulsed DC, based on the lower resistivity of decayed wood. In application, a hole is drilled in the pole and a wire probe inserted to serve as the electrode. Disadvantages of the technique are insensitivity to early decay and the masking effects of moisture content on resistance of wood.

Mechanical methods of assessing deterioration include either forcing a pin or drilling a hole into the material and measuring the force for a specific depth of penetration or the depth of penetration under constant force. Although the pin-based device is capable of sensing advanced decay, the disadvantages include insensitivity to intermediate decay and shallow penetration. One drilling technique reported in 1989 uses an air-driven, automatic-feed drill, with deteriorated material indicated when the feed rate of the drill changes. One disadvantage is the residual hole, which is a potential avenue for subsequent fungal infection, even if plugged. Another disadvantage of technique is that the drill bit has a tendency to follow checks that offer lower penetration resistance, thus allowing the drill bit to follow a path other than the desired one.

Prior art acoustic methods can be divided into sonic, stress wave, and ultrasonic, based on the frequency and method of wave excitation. Most of these techniques involve measurement of the effect on the material and/or the wave transmission path. B. D. Miller, F. L. Taylor, and R. A. Popeck, "A sonic method for detecting decay in wood poles," Proc. Am. Wood Preserv. Assoc. 61:109–115 (1965), describes velocities from impact-induced, sonic transmission across the grain of standing poles that were apparently sensitive to intermediate decay, although no data has been published.

Similar velocity measurements, but using piezo-electric transducers to induce signals, were also reported to be sensitive to decay in standing trees, by McCracken and S. R. Vann, in "Sound can detect decay in standing hardwood trees," Res. Pap. SO-195, USDA Forest Service, 6 (1983). In the same study, with a continuous sonic vibrator at 100 to 1000 Hz, the received signal showed an increase in amplitude in trees having substantial decay.

In a different approach by J. I. Dunlop, in "Testing of poles by using acoustic pulse method," Wood Sci. Tech. 15:301–310 (1981), impact-induced sound was propagated along the grain. However, it showed little or no sensitivity to decay in the damping coefficient and velocity. Dunlop also drove standing poles into longitudinal resonance by pulsing normal to the length on the top and in "pockets" along the height. With an input of 1 to 4 kHz, about 65% of decayed poles displayed signal irregularities.

The acoustic technique reported in the papers identified below is acousto-ultrasonics (AU), a method where AU was used to inject simulated stress waves in the ultrasonic range into a material and measure a single feature of the received waveforms. Using AU, M. Patton-Mallory and R. C. DeGroot, in "Detecting brown-rot decay in southern yellow pine by acousto-ultrasonics," Proceedings, Seventh International Nondestructive Testing of Wood Symposium, Pullman, Wash., pp.29–44, (1990) found that the frequency of the received waveform was sensitive to brown-rot decay, the major type of decay found in softwoods. In particular, the high frequency response of the transmitted waveform decreased in amplitude with an increasing degree of decay. R. L. Lemaster and F. C. Beall, in "The use of acousto-ultrasonics to detect advanced decay in round wood," Nondestructive Evaluation Center Report No. 35.02.01, University of California, Forest Products Laboratory, (1989) discusses the use of the ratio of the magnitudes of high to low frequency portions of the received waveform as an indicator of the possible degree of decay on small diameter logs.

SUMMARY OF THE INVENTION

The present invention provides a non-intrusive method and apparatus to detect bio-deterioration, and other conditions, in living trees and round wood materials with a high degree of reliability, when the condition is not very advanced, as well as when the condition is at a highly advanced stage. The apparatus of the present invention is also portable, compact and easy-to-use and calibrate to standardize the results from the same round wood subject, as well as between numerous such subjects.

A device of this type has major potential application by the utility industry to enable non-intrusive identification of utility poles that are in need of replacement. This will have several benefits to the utility company. One is that they will be able to maximize the use of the poles without fear of them falling and disrupting service, or posing a potential hazard to linemen climbing the poles, and they will not have to remove good poles as they do now on a routine basis to minimize the occurrence of just those problems.

Thus, the present invention will enable utility companies to make a number of readings at or below the base of the poles to any height, in order to characterize the internal characteristics of these poles along their length or height. As would be expected, the most critical portion of these poles from a safety, moisture and termite induced deterioration is near the ground surface, however, it is also possible for a utility pole to experience deterioration up the pole, even at the top, from weather elements and air borne termites.

With the present invention utility companies can determine the condition of the poles anywhere along their length, and develop a data base over time of the status of each pole to enable the tracking of minor deterioration to a point where it becomes more critical. The data base could also be used trigger the treatment of a pole that has experienced minor problems and to be assured as to the effectiveness of those treatments.

The present invention is used by securing a pulsing transducer and a receiving transducer to the pole, substantially diametrically opposite to each other so that the signal transmitted between them passes through the central portion of the tree or round wood material. In operation, the pulsing transducer transmits sonic and ultrasonic signals through the round wood, which propagate through possibly deteriorated areas within the round wood before being detected by the receiving transducer. The received ultrasonic signals are then processed to determine at least two signal parameters for analysis to determine the condition of the round wood in the vicinity of the transducers.

Also included in the present invention are several apparatus to secure the pulsing and receiving transducers to the round wood.

BRIEF DESCRIPTION OF THE DRAWINGS

The above and other features of the present invention and the manner of attaining them, will become apparent, and the invention itself will be best understood, by reference to the following description and the accompanying drawings.

DETAILED DESCRIPTION OF THE PRESENT INVENTION

Before discussing the present invention in detail it should be understood that the techniques, results and distinguishing procedures discussed below with respect to the detection of various conditions and forms of bio-deterioration extend to living trees, fallen trees, and round wood materials which may have been processed in a variety of ways. The fact that the following discussion is, by and large, with respect to round wood, and utility poles more specifically, is because of the practical nature of being able to detect bio-deterioration in that wood product. It is by no means to be assumed that the techniques and experiments discussed below, which are largely to utility poles, has any lesser value to living trees, fallen trees and other round wood materials.

Figure 1A:
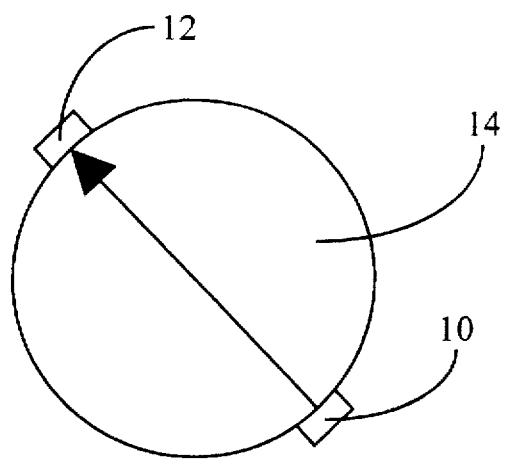
FIG. 1A schematically illustrates the positioning of a pulsing assembly and a receiving assembly around a sound utility pole, whereby the arrow indicates the direction or wave path of a signal from the pulsing assembly to the receiving assembly.
Figure 1B:
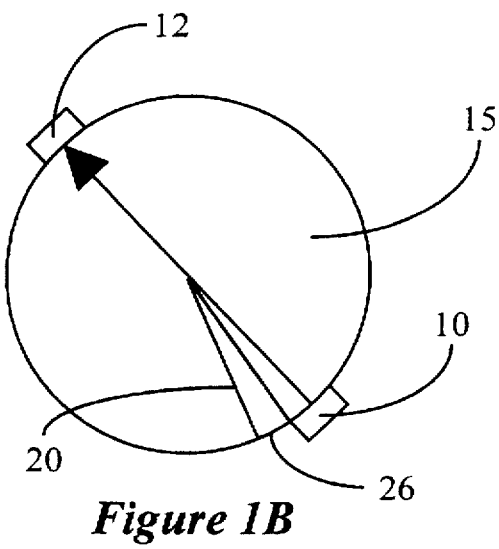
FIG. 1B schematically illustrates the positioning of the pulsing and receiving assemblies around a utility pole having a major check.
Figure 1C:
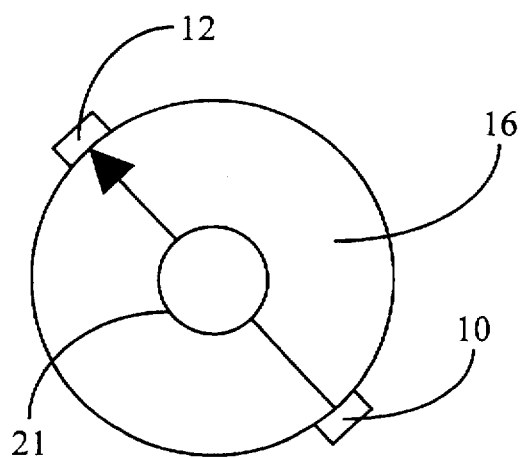
FIG. 1C schematically illustrates the positioning of the pulsing and receiving assemblies around a utility pole having deterioration in the center.

FIGS. 1A through 1D illustrate a pulsing assembly 10 and a receiving assembly 12, which form a part of an AU system according to the present invention, in position around four different round wood or utility poles 14, 15, 16, 17. Pole 14 is sound with no deterioration, pole 15 is sound with a major check 20, pole 16 has a deteriorating area 21 at its center, and pole 17 has a major check 22 and a deteriorating area 23 at its center. The examples illustrated in FIGS. 1B and 1D exemplify the most likely occurrences, and the examples in FIGS. 1A and 1C are included for completeness. For simplicity of illustration, the present invention will be described in relation to utility poles.

The present invention can be used on poles where there is no check, as well as on those that have experienced checks. With a pole like poles 14 and 16 in FIGS. 1A and 1C, pulsing assembly 10 and receiving assembly 12 are attached to the pole diametrically opposed to each other thereby maximizing the distance between each of them to ensure that the transmitted signal path passes through the central portion of the pole. Since it is possible for the pole to include an internal check or other grain separation that is not externally visible, and that from various experiments that are discussed below, it is known that internal check can effect the transmitted signal depending on the angle between that check and the transmitted signal, at least two sets of measurements are usually made on such poles. Those additional measurements are conducted by placing the pulsing and receiving assemblies 10 and 12 diametrically opposed to each other at other points around the circumference of the pole. If only one other measurement is made, pulsing and receiving assemblies 10 and 12 are typically displaced approximately 90° from the first location.

The proper positioning of pulsing assembly 10 and receiving assembly 12 relative to visible major checks 20 and 22 of poles 15 and 17, respectively, (see FIGS. 1B and 1D) is also an important aspect of the present invention. In order to properly position pulsing assembly 10 and receiving assembly 12, the major check 20, is visually located, and the edge 26 of major check 20 is identified. A convenient spot, in close proximity adjacent to edge 26 is selected for positioning pulsing assembly 10, typically, approximately 25 mm from edge 26.

Pulsing assembly 10 is secured to pole 15 and receiving assembly 12 is also secured to pole 15 in a position diametrically opposite pulsing assembly 10 for the same reason discussed above for poles without a major check. The pulsing assembly 10 is oriented toward the receiving assembly 12 and the center of pole 15, such that the signals emitted by pulsing assembly 10 do not propagate through major check 26, otherwise, the received signals will be delayed and attenuated, which also happens to a lesser degree for hidden checks.

Figure 1D:
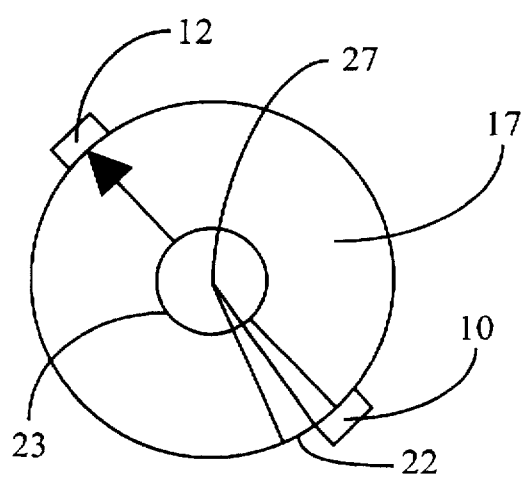
FIG. 1D schematically illustrates the positioning of the pulsing and receiving assemblies around a utility pole having a major check and deterioration in the center.

As illustrated by the signal orientation arrow in FIG. 1D, pulsing assembly 10 and receiving assembly 12 are oriented such that the transmitted signals pass through deterioration area 23. Since there is a high probability that if deterioration is present, it would be near the tip 27 of major check 22, the recommended orientation of pulsing assembly 10 and receiving assembly 12 will increase the probability that the signals will propagate through the deterioration area 23, but not through major check 22.

The objective of the AU system of the present invention is to simulate stress waves without disrupting the round wood material through which the AU waves propagate. Once launched inside the material, the AU waves are modified by stochastic processes like those that affect spontaneous acoustic emissions from internal sources during stressing or deformation. For example, if the material has a lower modulus, then it will affect the characteristics of the AU waveform, by reducing its amplitude and high frequency components. Thus the received signals will provide indications as to the existence of unusual obstacles, such as bio-deterioration, along the wave path.

Figure 2:
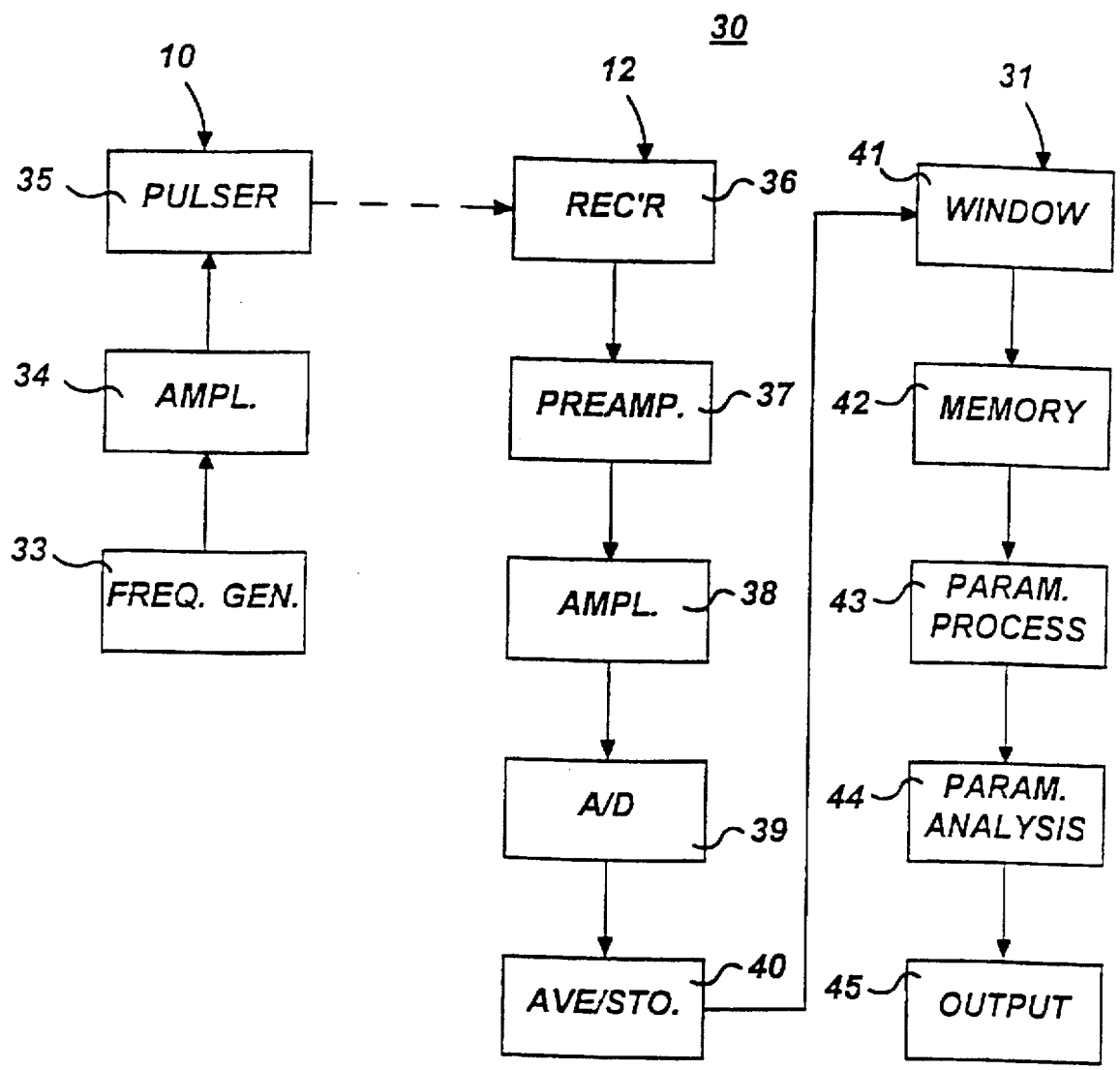
FIG. 2 is a block diagram of the inventive bio-deterioration detection and processing AU system comprising the pulsing and receiving assemblies of FIGS. 1A through 1D.

FIG. 2 is a block diagram of the AU system 30 constructed according to the present invention. The AU system 30 generally includes the pulsing sub-system 10, the receiving sub-system 12 and a signal processing sub-system 31. The pulsing sub-system 10 includes a frequency generator 33, which generates the desired input signals; an amplifier 34, which is basically a power amplifier to amplify the input signals to a desired energy level for pulsing the transducer to inject signals into the desired pole, e.g., 17; and a pulser or pulsing transducer 35. (Sample model numbers of each of these units is given below in the section entitled "Experimental Configuration and Results").

Considering now the frequency generator 33, it can generate an input frequency that is largely in the ultrasonic range but can also extend from the audio range to the ultrasonic range. Typically, the upper range of the input frequency is around 150 kHz, and the main limitation on the upper frequency limit is the sensitivity to be generated. It should however be clear to those skilled in the art that higher frequencies can be used. The lower frequencies can be below 10 kHz, and are typically in the range of 30 kHz.

The frequency range or pattern of the signals generated by frequency generator 33 can include any of the following:

1. Single frequency either high or low;
2. A selective arbitrary choice of high or low frequency;
3. Two or more discrete frequencies sequentially; and
4. Incrementally scan an entire frequency range.

A combination of these, and other signal patterns could also be used in a sequential combination. Wherein, each transmission increment is continued until a predetermined number of periods of the signal are captured at the same frequencies. One way that this could be assured is to set the increment time of collection at each frequency to the maximum transmission time through the pole, which is very short relative to the total analysis time.

The pulsing transducer 35 is generally similar to a receiver or receiving transducer 36 which forms a part of the receiving sub-system 12, and can be any one of following three types of transducers, with the understanding that a combination of more than one type of transducers can alternatively be used, and that more than one pulsing and one receiving transducers can be used:

1. Resonant transducer. This type of transducer typically produces the highest voltage output signal at the resonant frequency of the transducer.
2. Slightly damped transducer. In this type of transducer the output voltage response at the resonant frequency of the transducer is lower than the voltage response at frequencies adjacent the resonant frequency in order to increase the voltage response level on either side of the resonant frequency.
3. Broadband transducer: This type of transducer ideally presents a fully uniform output voltage response in the frequency range of interest.

(As stated above, sample model numbers of each of these units is given below in the section entitled "Experimental Configuration and Results" and they are typically Piezoelectric type transducers)

Considering now receiving sub-system 12 (FIG. 2), it includes a receiving transducer 36, a preamplifier 37, an amplifier 38, an analog-to-digital converter 39, and a average/store processor 40. If receiving transducer 36 were a resonant transducer, the primary signal output is the resonant signal that is characteristic of that transducer model as modified by the amplitude, frequency and wave components of the incoming signal. On the other hand, if receiving transducer 36 were a broadband transducer, then it would reflect the frequency content of the incoming signal.

Pre-amplifier 37 has several general functions, including the amplification of the signal from receiving transducer 36 to maximize the signal-to-noise ratio. For example, a very wideband filter is used that is broad enough to maintain the frequency content of the signal, particularly to facilitate processing of the signal in the frequency domain. In general, pre-amplifier 37 provides a gain between 40–60 dB, and amplifier 38 provides a gain on the order of 40 dB. Analog-to-digital converter 39, in turn, samples the analog signals from amplifier 38 at a rate that is high enough to accurately retain the frequency and amplitude content of the analog signals. It was discovered in experimentation that a sampling rate on the order of 1 MHz achieves that result. Average and store processor 40 next processes the digitized signals from A/D 39 by averaging typically 200 waveforms, and then stores those average values.

The signal processing sub-system 31 generally includes windowing discriminator 41, however it is optional, to control the time/frequency/amplitude portion of the signals from average and store processor 40 to be analyzed. The windowing feature provides the ability to select one or more windows of predetermined size or sizes (i.e. range of time, band of frequency, or range of amplitudes), and is used to process the signals and to enhance the relationship of the signal to the change in the signal parameters. Each individual parameter is preferably windowed differently from the other parameters.

The windowing feature, when included enhances the parameters of interest of the signal from receiving sub-system 12 to improve the sensitivity of the overall system to be able to determine if and when deterioration is present. For various reasons the windowing that is performed can take different forms, depending on the result that is desired or the condition that has to be overcome. For purposes of discussion here, time windows will be discussed, however, it should be understood that similar windowing can be performed in frequency and amplitude, or windowing in some instances may be done in two or all three domains.

More specifically, what is collectively referred to as windowing consists of three different, each optional, functions. First, what has been referred to above as amplitude windowing is noise filtering which is discussed more completely below with respect to FIG. 11. Second, what was described above as time windowing is time bracketing of regions of the received signal to enhance the analysis of the data for various parameters as discussed more completely below with respect to FIGS. 11 and 14. Third, what has been referred to above as frequency windowing is the use of bandpass or comb filters to enhance discrimination between a sound pole and a pole that contains defects as described more completely below with respect to FIGS. 4, 6 and 11.

Figure 14:
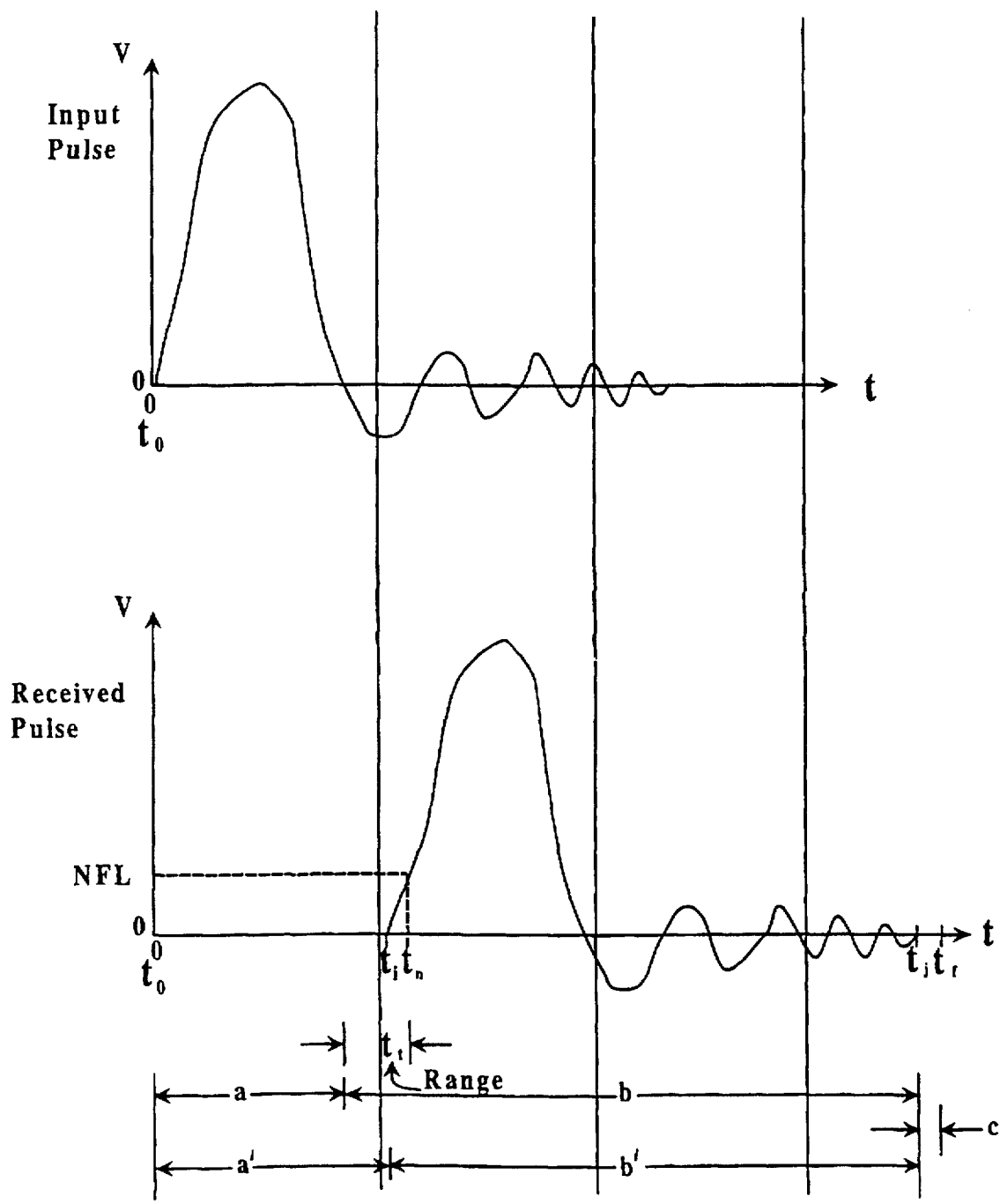
FIG. 14 illustrates various time windows that may be used to enhance various signal parameters by accepting the data only during a fixed period of time.

FIG. 14 illustrates various time windows with respect to a pulsing transducer input signal and a signal received by a receiving transducer. At time $t_0$ an input signal is applied to the pulsing transducer that is then applied to the round wood and is transmitted therethrough having an estimated transit time, $t_r$. $t_r$ can be determined from three factors: the apparent velocity of the signal; the length of the signal path through the wooden item; and the type of wood being tested. The actual arrival time of the signal at the receiving transducer is labelled as $t_i$, however, if noise filtering has been employed prior to the time windowing, the received signal will not be detectable until $t_n$ with $t_j$ being calculated from the signal level and slope at $t_n$. $t_j$ is the time at which the received signal again falls below the noise filter level, or substantially to zero if noise filtering is not employed. One other time that is of interest in time windowing is a selected time following $t_j$, that is identified as $t_f$ in FIG. 14.

When $t_f$ is estimated, the value will fall within a range above and below $t_i$ as shown in FIG. 14 (i.e. $t_f \approx t_i$). In those situations, to insure that no portion of the received signal occurs in the transmission time window, a or a' of FIG. 14, a user selected value, $\epsilon$, is subtracted from $t_f$ in defining the closure time of window a (i.e. to insure that $t_f - \epsilon \leq t_i$ since $t_f$ can be greater than, equal to, or less than $t_i$). The necessary value of $\epsilon$ is based on the signal velocity through the material being tested which can be affected by several factors (e.g. moisture content, internal knots, wood density, etc.). With experience the user will be able to make an effective choice of the value of $\epsilon$. One way that $\epsilon$ can be selected is for the system user to make an initial choice of a value for $\epsilon$ and to observe the resultant received signal at the test site. Then, based on that resultant signal an effective value for $\epsilon$ can be selected so that $t_f - \epsilon \approx t_i$.

Several window definitions have been found helpful in determining various signal parameters more accurately and they are illustrated in FIG. 14 and in

TABLE I

| WINDOW | a | a' | b | b' | c |
|---|---|---|---|---|---|
| OPEN | $t_0$ | $t_0$ | $t_i - \epsilon$ | $t_i$ | $t_j$ |
| CLOSE | $t_i - \epsilon$ | $t_i$ | $t_j$ | $t_j$ | $t_f$ |

Note that a' and b' are determined through the use of noise filtering, whereas a and b are estimated when noise filtering is not used.

For example, a first option might be to use a fixed window length, a, that is shorter than the normal transit time of the signal through the wooden item. One way to define the length of a window using this option, is to open the window for a fixed period starting at the initial signal capture time (time=0) when pulsing sub-system 10 begins to transmit a signal and then close the window at a point in time that is equal to the expected transit time of the signal through the wooden item plus the time to collect enough cycles of the signal to capture a full initial portion of the transmitted signal.

Figure 3:
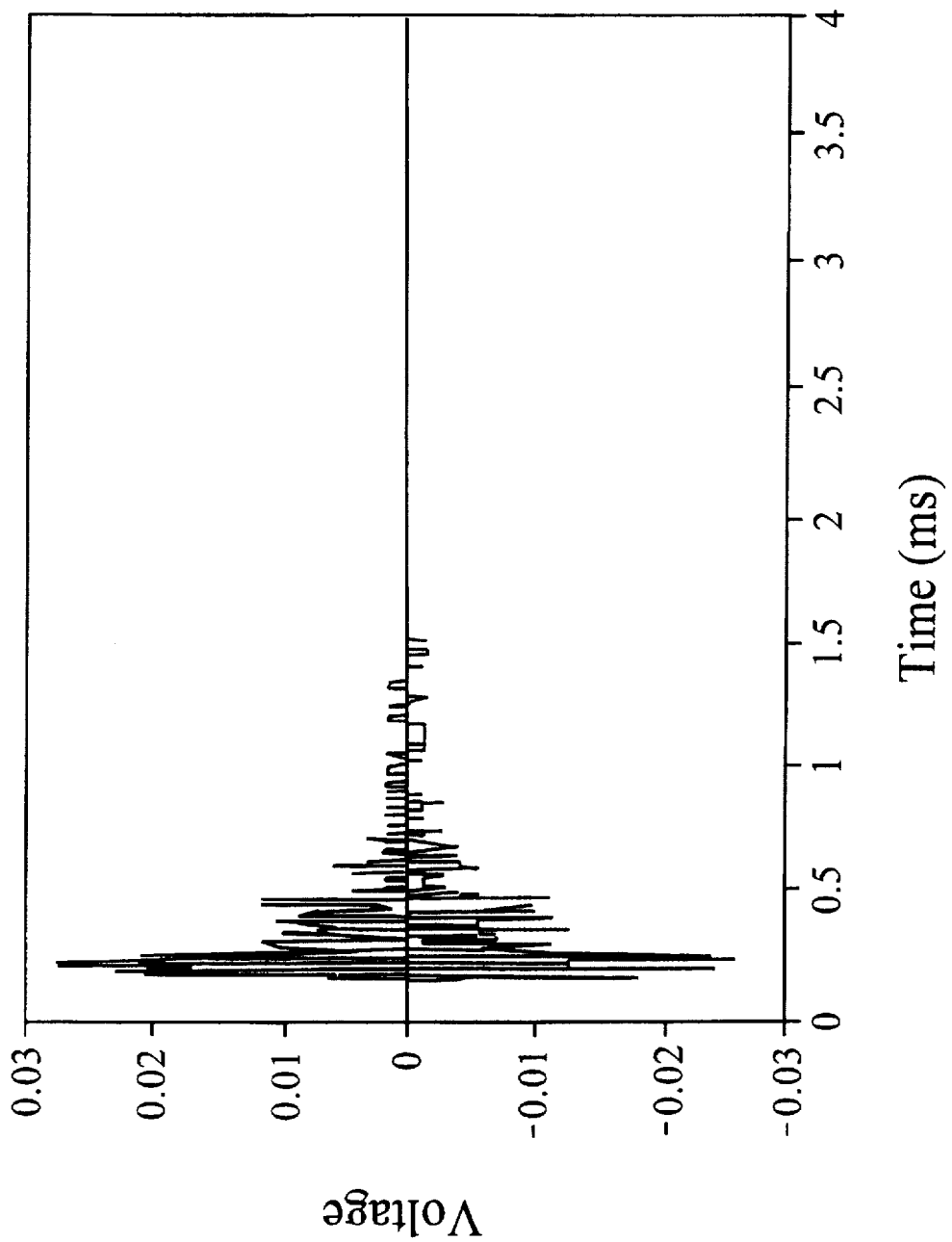
FIG. 3 is a typical waveform of a 120 kHz signal that passes through the sound utility pole of FIGS. 1A or 1B, showing a high initial amplitude and an exponentially decaying signal.

Referring to FIG. 3, window a would be from 0 ms to approximately 0.7 ms for a sound specimen. Thus, if a signal is delayed because of a longer signal path, such as around a deteriorated or hollow area of the pole being tested, that signal may not appear in a window defined in this way. Also, it has been noted experimentally that signals appearing in a window defined in this way generally have a strong high frequency component.

Another way to select the length of a window in option one is to start the window at the time that the initial wavefront of the transmitted signal reaches receiving sub-system 12, $t_i$, (approximately 0.2 ms in FIG. 3) and to close the window at a point that is similar to the point of closure discussed above for the first approach.

As mentioned above, multiple windows can also be used. For the above two examples, an additional window could be formed to include the tail, or a suitable portion of the tail, of the received waveform that occurs after the first window is closed. When this technique is applied, a comparison of the AU signal parameters, in both time and frequency domains, for both windows, can be performed and thus enhance the sensitivity of the signal parameters to bio-deterioration within the material. There are other windowing techniques that could be employed, including a series of multiple windows from which the AU signal parameters can be extracted and classified relative to the characteristics of a signal through a sound pole.

A second option is to open a window in close proximity to the time of first arrival of the signal at the receiving transducer, $t_i$. The window can then be closed after a fixed time or after the trailing edge of the signal is detected, $t_j$ or $t_f$.

The signal portions passing through the selected window, or windows, are then stored in memory 42, and the parameters of those stored signals are then processed by parameter processing software 43, analyzed by parameter analysis software 44, and the results of the parameter analysis put into a report for delivery to an output device symbolized by block 45.

There are several approaches that affect or relate to signal processing. Greater sensitivity is obtained by using a resonant receiving transducer 36, however, the use of a broadband receiving transducer 36 provides the best possible frequency response. The time domain or the frequency domain can be used depending on which AU parameter is of interest. If the frequency domain is used in signal processing, then a broadband transducer would be the preferred choice. If, on the other hand, the time domain signal is used, the resonant transducer would be the preferred choice.

In parameter processor 43, signals are typically processed in two domains: time and frequency. In the time domain, the processed signal is the same as that in memory 42. The following three time domain parameters are utilized:

1. RMS. The root mean square of the average signal is processed for determining the average voltage of the entire signal, which is then converted to a single voltage value.
2. Velocity. The velocity is determined by measuring the time of first arrival of the signal and then dividing that time by the distance between the pulsing and receiving transducers 10 and 12. Consequently, it is not true velocity, but rather the apparent velocity since the actual path of the waveform is not known.
3. Centroid time.

The frequency domain analysis requires the intermediate step of converting the signal from the time domain to the frequency domain. This conversion is done using FFT (Fast Fourier Transform) by parameter processor 43. There are also a number of frequency domain parameters, two of which are:

1. Centroid frequency.
2. Third moment.

A reference that discusses each of those time and frequency parameters is Kiernan, M. T. and J. C. Duke, "1988 PC analysis of an acousto-ultrasonic signal", Materials Evaluation, 46:1344–1352.

The foregoing are the five time and frequency domain parameters used by the present invention to identify various defects in a wooden item. Using these five parameters, experimental results have shown that moisture content, chemical treatment, wood features (e.g. knots), and wood grain discontinuities (e.g. checks and splits) can be distinguished from various forms and degrees of deterioration of the wood which is not possible by using only one signal parameter. It should however be understood that additional parameters, and combinations of parameters, can also be selected and analyzed in other domains, such as the phase domain. Other parameters can also be selected and analyzed in each of the time and frequency domains.

The parameter analysis can be done in a variety of ways including the preparation of look-up tables similar to Table II described below, in which the five time and frequency domain parameters identified above are listed and correlated for each of the conditions that are sought to be identified. Criteria can be established, either empirically or mathematically for each parameter, and determination made as to whether or not these parameters fit within particular ranges.

Alternatively, some or all of these parameters can be weighted in accordance with the determination being sought. For instance, if the determination relates to the sensitivity to smaller bio-deteriorations, then the RMS, centroid frequency and third moment parameters are given greater weight than the other parameters. If, on the other hand, the determination relates to the degree of deterioration, then the velocity and centroid time parameters are given greater weight than the other parameters.

There are special conditions of wooden poles that can be detected from combinations of the values of AU signal parameters. For example, a hollow pole has a unique combination of values of the apparent velocity, RMS, and frequency centroid parameters that distinguish it from a sound pole. In another example, if a pole has a hidden major check that covers most or all of the cross section in the transmission path, the RMS parameter of the output signal would be similar to the RMS parameter of an output signal for a substantial decayed pole; whereas, the signal velocity would distinguish between a pole with a hidden check and a substantially decayed one, but does not distinguish between a sound pole and a pole with a hidden major check. As a further example, a pole with high moisture content reduces the signal velocity through the pole, which would normally be an indicator of deterioration, however, if the time centroid parameter varies very little from the values for the time centroid parameter for a sound pole the high moisture content pole can be distinguished from a pole having interior deterioration. Conversely, a pole that is heavily checked shows little difference in signal velocity from a sound pole, however, such a pole shows an increase in the time centroid parameter from that expected for a sound pole.

Thus, the present invention presents several important features, including but not limited to the proper positioning of the pulsing and receiving transducers 10 and 12 relative to the poles. Additionally, it is now possible, using the sensitivity of specific parameters, to identify the presence and degree of deterioration of a wooden pole. The parameter processing and analysis features of the present AU system 30 provide the ability to discriminate very early stages of decay, or to provide an output that would indicate the degree of deterioration.

Figure 4:
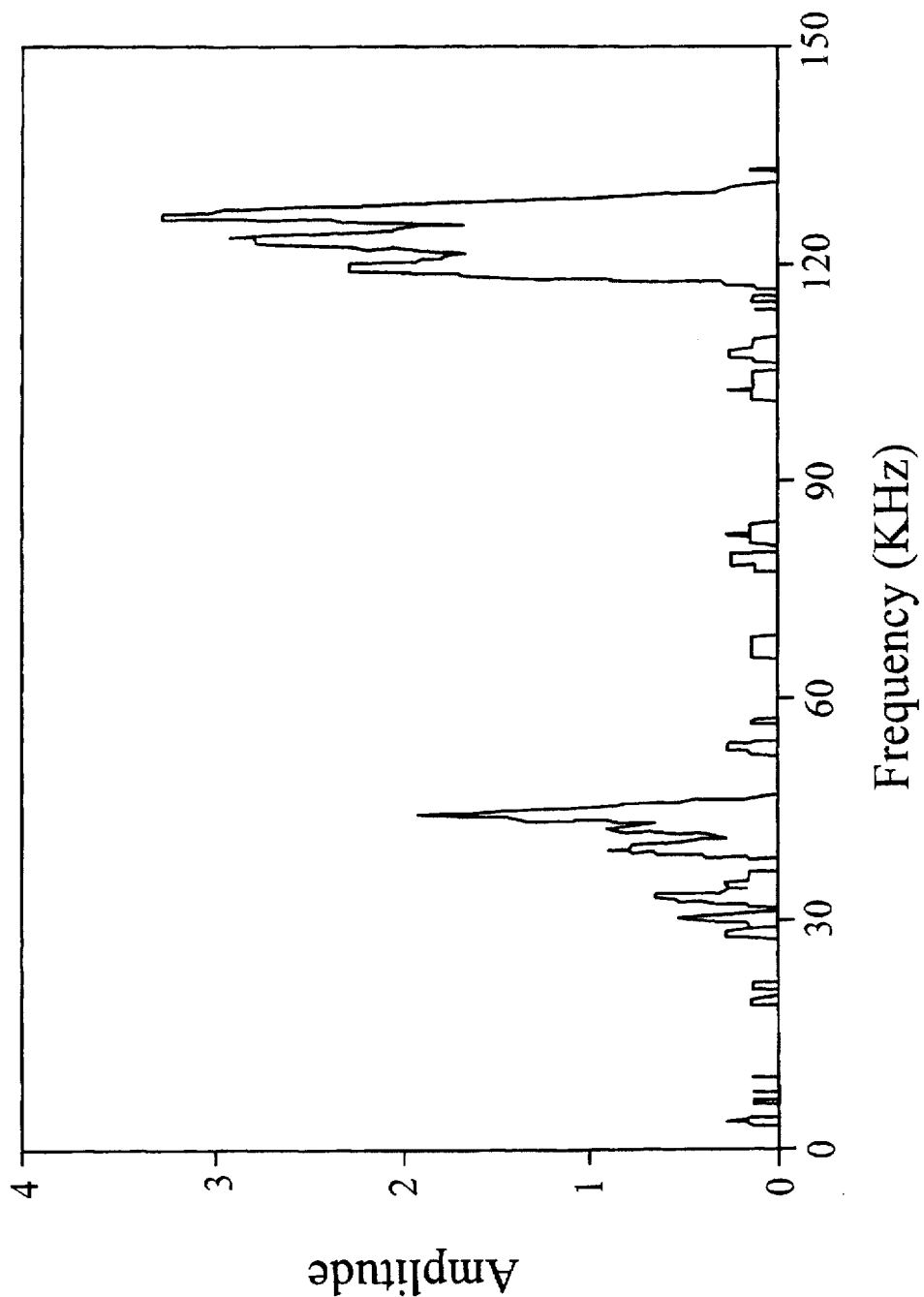
FIG. 4 is a typical frequency spectrum of a signal showing that the pulsing frequency of 120 kHz passes through the sound utility pole of FIGS. 1A or 1B.

FIG. 3 is a waveform that has passed through a sound utility pole 14 of FIG. 1A, showing a high initial amplitude and an exponentially decaying signal amplitude. This waveform shows that sound material has little effect on the amplitude, shape and frequency content of the signal propagating therethrough. A reference waveform of this type can be obtained from a sound part of a pole to be tested and then compared to signals from other parts of the pole suspected to contain some degree of deterioration. FIG. 4 is a frequency spectrum showing a received signal with a 120 kHz component that was contained in the signal that the pulser applied to a sound utility pole 14 of FIGS. 1A or 1B and which was attenuated very little as a result of the signal transition through the pole. This frequency spectrum could also be the basis of windowing and used in conjunction with time windowing based on the waveform shown in FIG. 3 to eliminate extraneous noise, etc.

Figure 5:
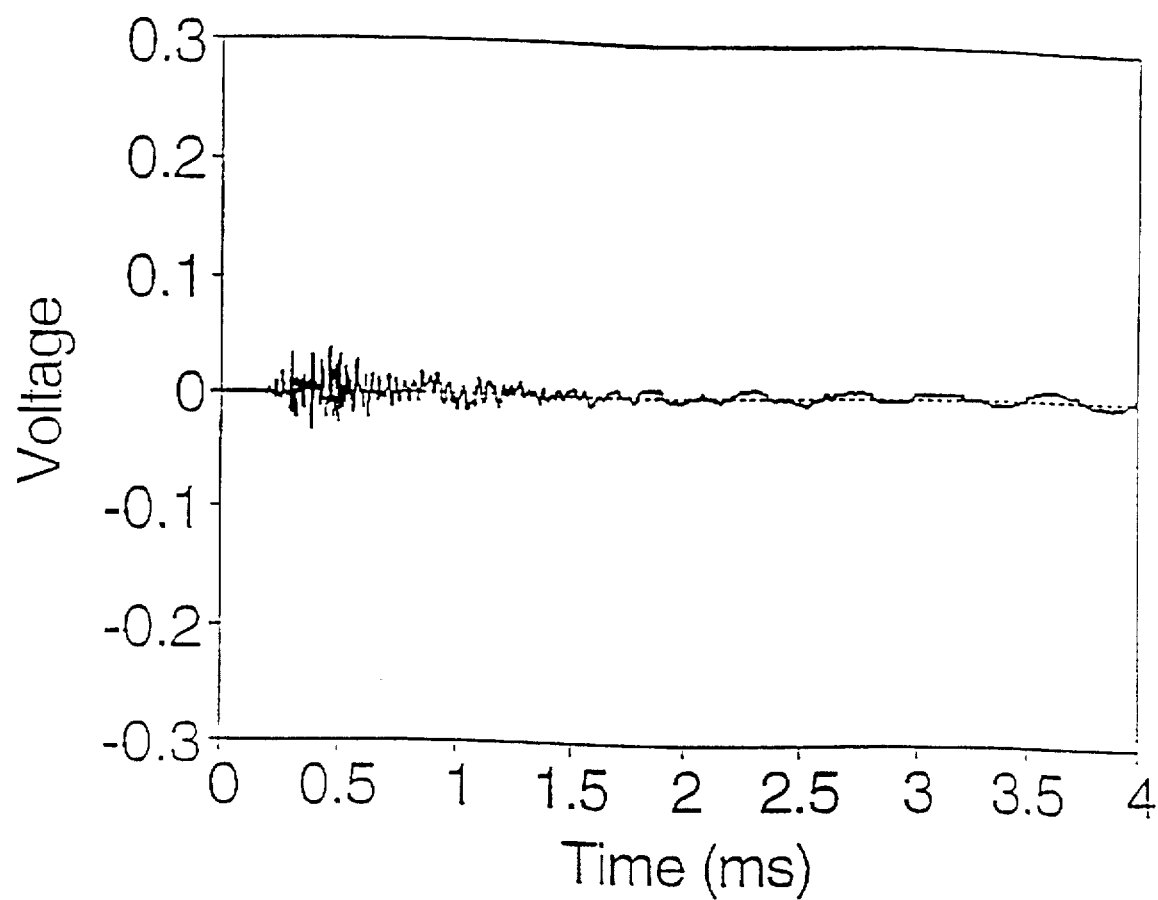
FIG. 5 is a typical waveform of a 120 kHz signal that passes through a utility pole of FIGS. 1C or 1D with a reasonable amount of deterioration in the signal path.

FIG. 5 is a timing graph showing the characteristics of the utility pole 16 of FIGS. 1C or 1D, with a reasonable amount of deterioration in the signal path. The key determination is whether deterioration exists in the material which affect the amplitude, frequency content and other waveform domains of the signal propagating through pole 16. The received signal is processed to develop the AU parameters of interest as discussed above from which the presence or degree of deterioration in the material can be determined. This determination can be done on an absolute basis or on a relative basis (comparison to waveforms in a sound pole illustrated in FIGS. 3 and 4).

Figure 6:
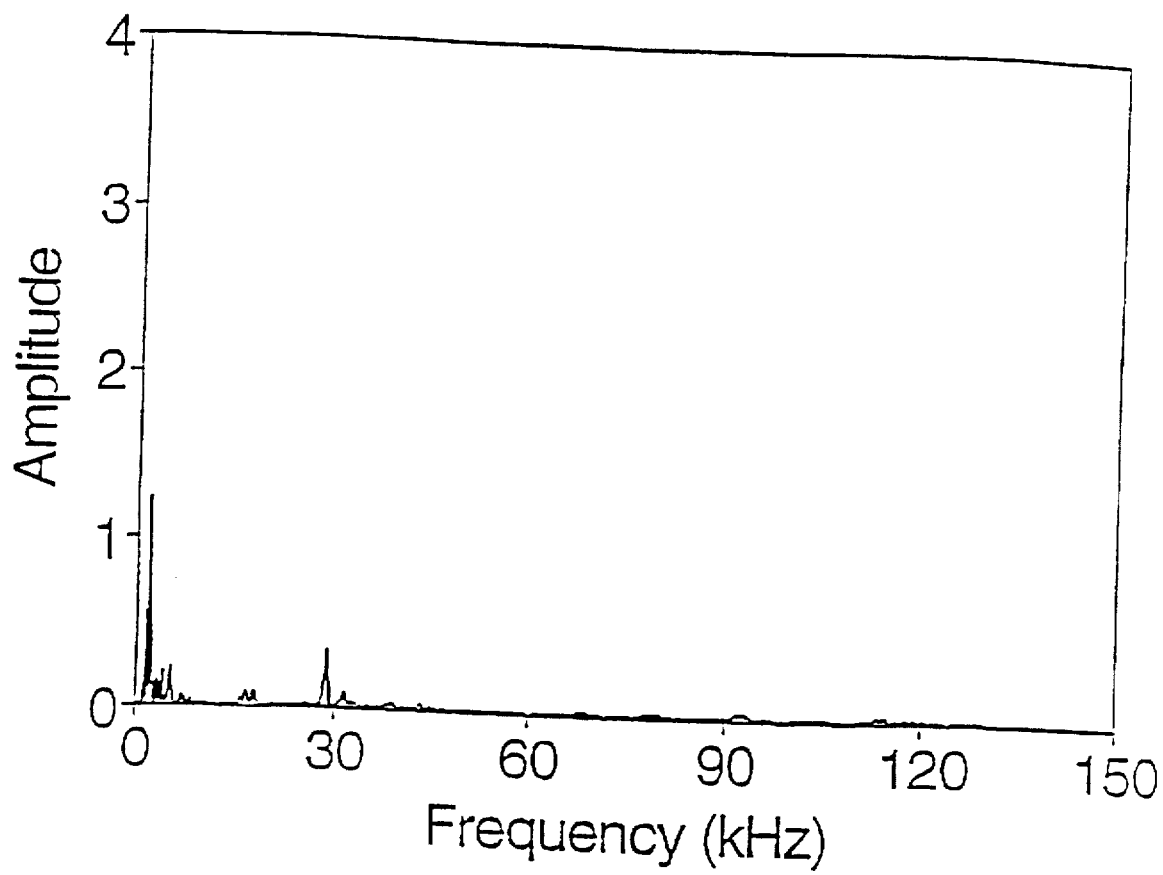
FIG. 6 is a typical frequency spectrum of a 120 kHz signal showing the characteristics of the utility poles of FIGS. 1C or 1D.

FIG. 6 is a frequency spectrum showing the characteristics of the utility poles of FIGS. 1C and 1D. This frequency spectrum shows the high frequency content of the signal is highly attenuated in deteriorated material.

One of the techniques for preparing the received signal to accurately determine some of the signal parameters of interested, as discussed below, is what is referred to herein as frequency windowing". For example, viewing FIGS. 4 and 6 for a sound pole and a decayed pole, respectively, band pass filters, or a comb filter, that passes frequencies in a narrow range around 40 kHz and 130 kHz could be applied to the received signal. Thus, high amplitude signal components from the filter would be observed for a sound pole (see FIG. 4), while zero or noise signal levels would be observed for a decayed pole (see FIG. 6). Further discussion of frequency filtering, and the relation of noise filtering and time windows thereto are discussed below, particularly with respect to FIG. 11.

Figure 10:
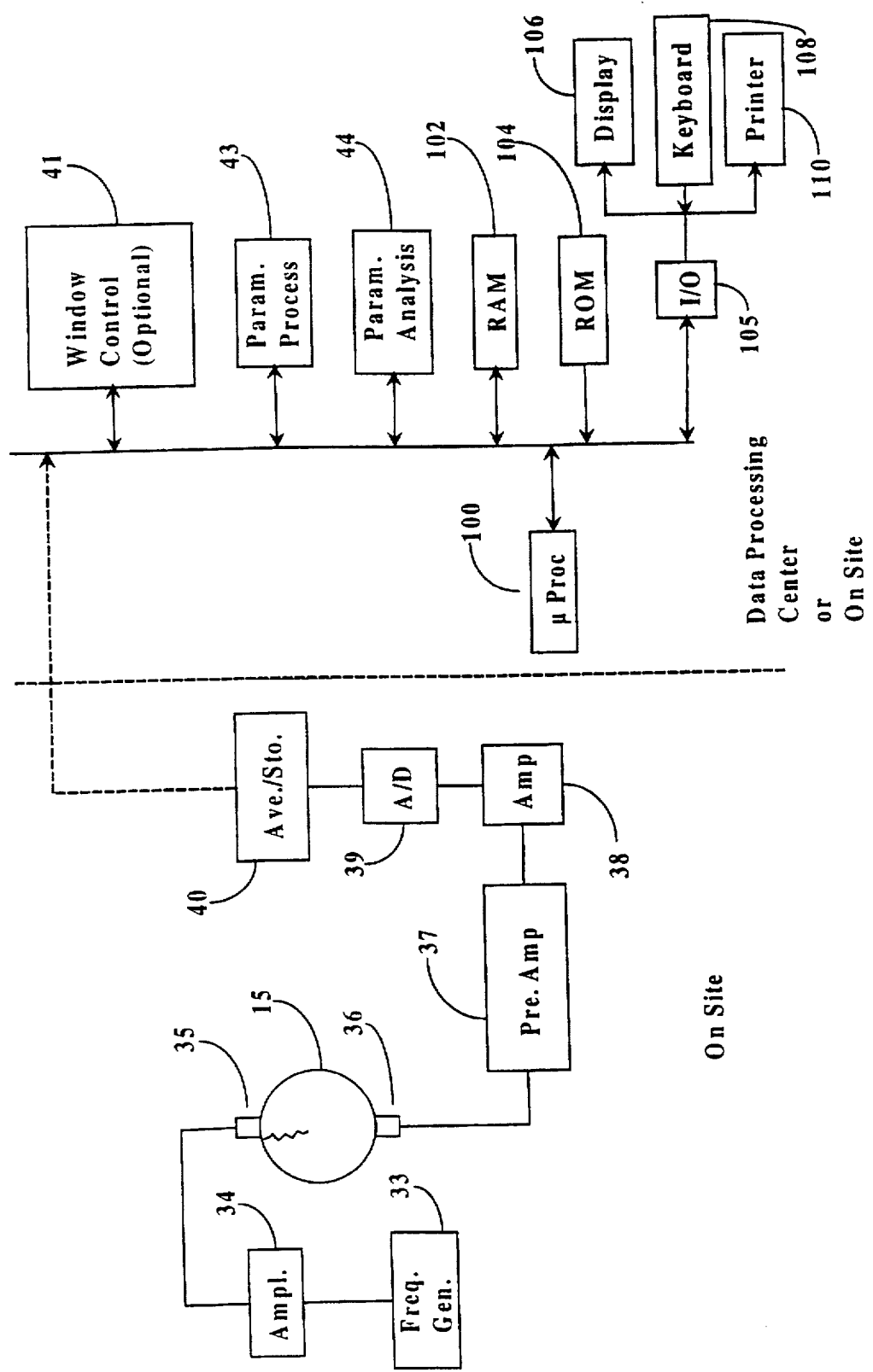
FIG. 10 is a schematic block diagram of the system of the present invention.

FIG. 10 is block diagram of a system capable of implementing the flow of the functional block diagram of FIG. 2. Here, the system is shown in two parts: the on-site portion which is equivalent to the pulsing sub-system 10 and receiving sub-system 12; and the data processing portion which is equivalent to the signal processing sub-system 31. Given the current state of the necessary electronics to implement this system, the majority, if not all of the data processing center can be combined with the on-site portion in a relatively small package.

The on-site portion is substantially the same as a combination of FIG. 1A and the pulsing and receiving sub-system 10 and 12, respectively, columns of FIG. 2. The data processing portion, or signal processing sub-system 31, is shown here implemented with a micro-processor 100 in communication with a variety of other components via a data bus. The usual support components, namely RAM 102, ROM 104 and I/O 105 are connected to the data bus, as are the optional window control 41, parameter processor 43 and parameter analyzer 44 from the signal processing sub-system 31, and the average/store processor 40 of receiving sub-system 12, all of FIG. 2. Additionally, standard I/O devices display 106, keyboard 108 and printer 110 are shown connected to I/O 105. Other I/O devices could also be similarly interfaced as necessary, e.g. a fax/modem.

Figure 11:
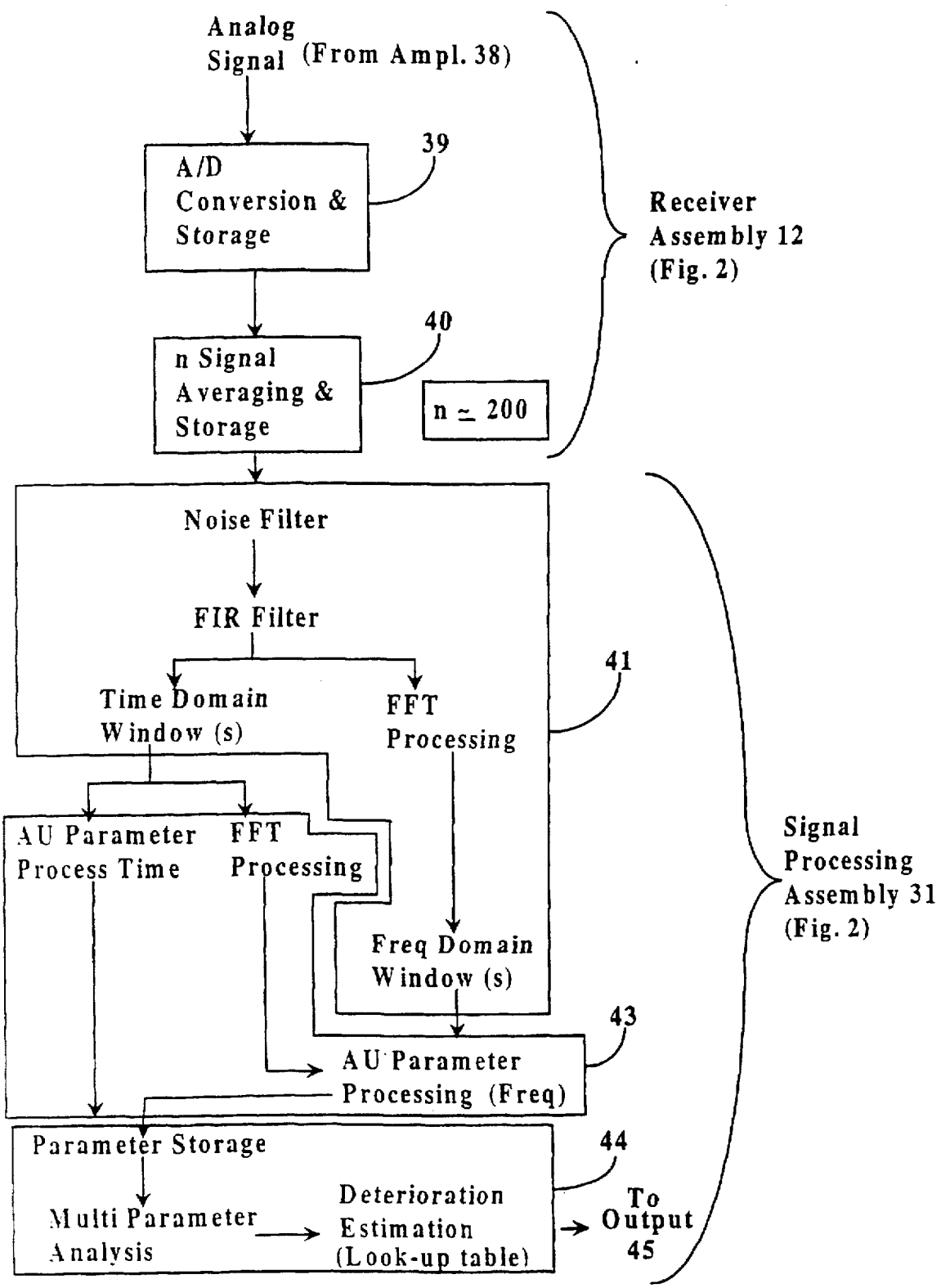
FIG. 11 is a flow chart of the signal processing of the present invention.

FIG. 11 is one processing flow chart that might be used to implement the present invention on a system like the one shown in FIG. 10. Since FIG. 10 is broken into two sections: an on-site section and a data processing section, the flow chart of FIG. 11 is similarly divided to illustrate operation of the block diagram implementation of FIG. 10. As stated in the discussion of FIG. 10, the entire system could be implemented into a single on-site unit.

The input signal to the flow chart of FIG. 11 is the analog signal from amplifier 28 on which an A/D conversion is performed followed by the digital signal being stored (block 39). The next step averages n (perhaps 200) of the signals stored following the A/D conversion as discussed above and then stores the resultant averaged signal (block 40). Block 41 illustrates various filtering, or "windowing", operations that are performed on the averaged signals from block 40. Here, the signal first undergoes noise filtering with the resultant noise filtered signal next applied to a Finite Impulse Response (FIR) filter. The output signal of the FIR filter is then used to develop both the time and frequency parameters that were discussed above. For the time parameters, the next step listed is the optional time domain windowing operation discussed above. For the frequency parameters, the digital time domain signal from the FIR filter undergoes FFT (Fast Fourier Transformation) processing to convert the signal to the frequency domain, and that frequency domain signal is next subjected to the optional frequency domain windows discussed above.

The operation on the two signals developed in block 41, namely the time domain and frequency domain signals, are then applied to block 43. The time domain signal, which may have been subject to windowing, is operated on twice, to develop the time domain parameters of the signal (RMS, velocity and centroid time as discussed above), and to apply the windowed time domain signal to FFT processing to generate a time windowed frequency domain signal. That time windowed frequency domain signal and the frequency windowed frequency domain signal from block 41 are operated on in block 43 to generate the frequency domain signals (centroid frequency and third moment as discussed above). From here the processing flow continues with block 44 where the time and frequency domain parameters are stored, as necessary, and then they collectively undergo multiparameter analysis which can be performed with an experimentally determined look-up table to identify the estimated deterioration status of the round wood object that was being tested within the range of that individual test. To assure the status of the round wood object, it may be necessary to test that object are various locations along the length thereof.

The noise filtering step of block 41 is performed to enhance the determination of both velocity (transit time) and the calculation of the other AU parameters of interest. In doing so the accuracy of the velocity is improved by reducing the probability of noise being identified as the received signal prior to the normal arrival time of the leading edge of the received signal by transducer 36. In this step, the stored averaged received signal is analyzed for approximately two thirds of the typical transit time from transmitter 35 to receiving transducer 36 with the highest amplitude of the noise in this time period being identified and a signal threshold for use during the true signal reception period being adjusted above that threshold by a factor of 1.1 to 3 times the peak noise level. The received signal after the time period during which the noise threshold is set is then reprocessed to identify the leading edge of the first crossing of the established noise threshold by the received signal. Due to the threshold that was established, the point at which the leading edge of the received signal exceeds that threshold occurs slightly later than the actual arrival time which would have been detected if the threshold level where set to zero and there was no noise. Thus a back-stepping calculation is made to identify the true signal arrival time based on the slope of the leading edge of that signal and the selected threshold level. It was found during tests of the present invention that with a sampling rate that is ten times the highest frequency within the received signal, this technique is sufficiently accurate for the application of the present invention. Thus, by performing noise filtering, the accuracy of the determination of the actual arrival time and the resultant calculated velocity is greatly improved from results obtained during experimentation where noise filtering was not used. Additionally, noise filtering removes extraneous time, frequency and other domain signals that could distort the calculated values of the other time and frequency parameters of interest.

Figure 8:
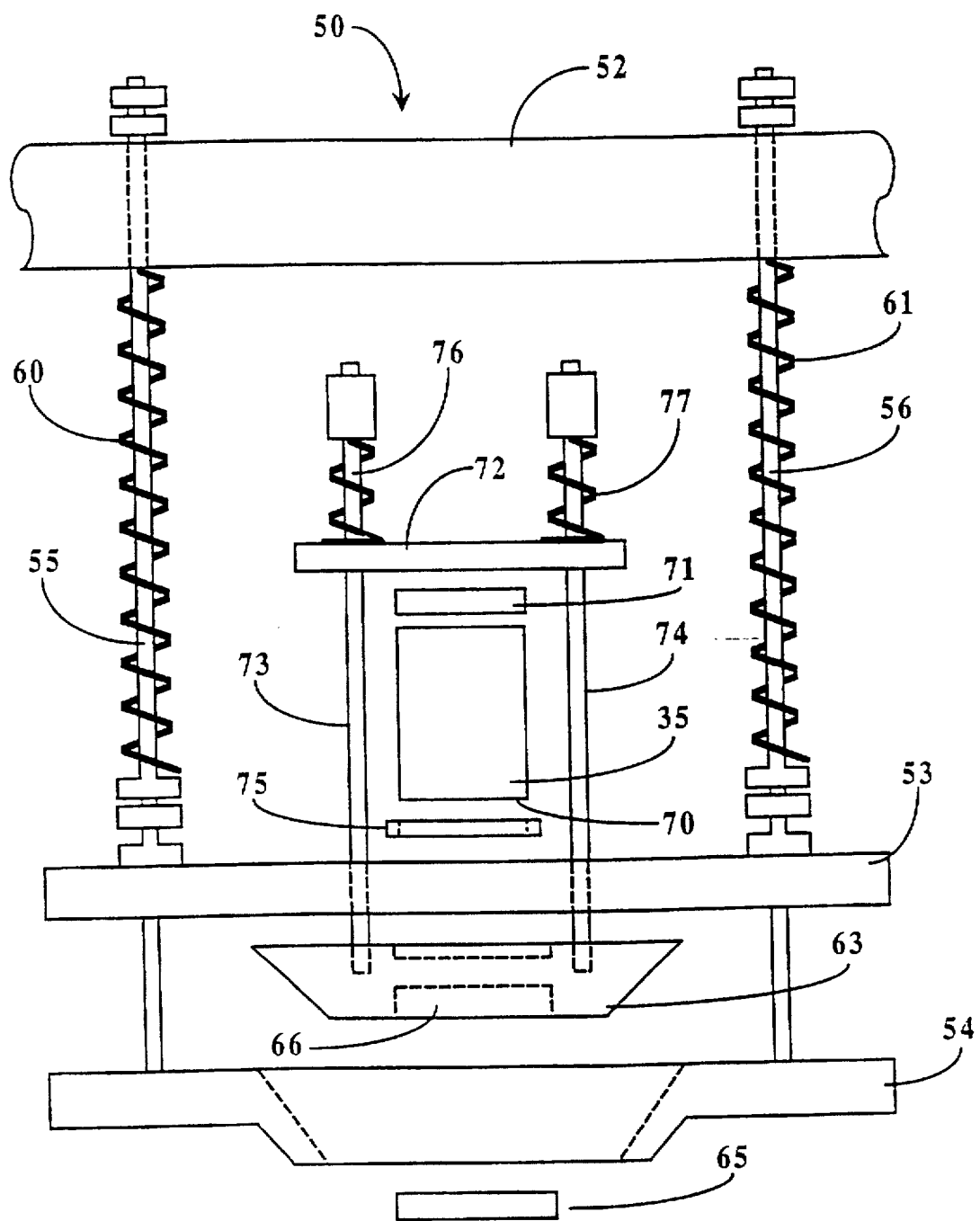
FIG. 8 is an enlarged partly exploded schematic view of a first mounting assembly used to secure a pulsing or a receiving transducer to the pole being investigated.
Figure 9:
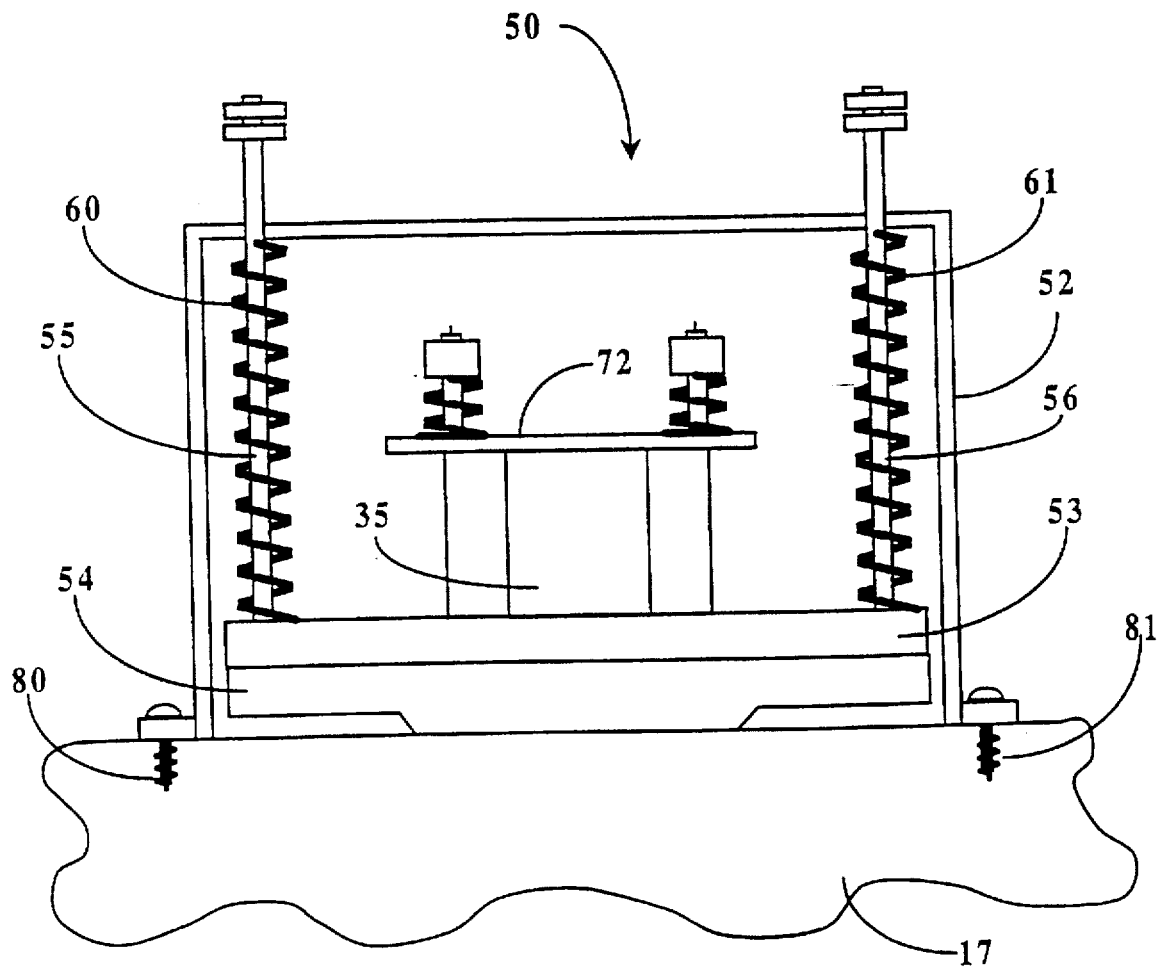
FIG. 9 is schematic view of the first mounting assembly of FIG. 8 shown secured to a pole.

FIG. 8 is partly exploded schematic view of one form of a coupling assembly 50 that can be used to secure the pulsing transducer 35, or the receiving transducer 36, to the pole being investigated. The coupling assembly generally includes a rigid, footed, open box frame, or housing, 52 with a hole through each foot to permit a screw to pass therethrough for attachment to the round wood of interest as illustrated in FIG. 9. The proximal ends of at least two rods 55 and 56 extend unencumbered through holes that are a larger diameter than rods 55 and 56 in the upper portion of frame 52. To prevent rods 55 and 56 from coming free of frame 52, a lock nut has been placed on the proximal ends of rods 55 and 56. At the distal end of the at least two rods 55 and 56, rods 55 and 56 are securely fastened to lower plate 54. Additionally, at a point on rods 55 and 56 spaced-apart from, and closest to, the distal ends of rods 55 and 56, rods 55 and 56 also pass through plate 53. Two or more springs 60 and 61 are mounted around rods 55 and 56, respectively, between frame 52 and metal plate 53 in order to apply a consistent biasing force to plate 53.

Plate 54 defines a tapered circular hole therethrough (shown dotted). A waveguide base 63, in turn, is a circular tapered disk that is sized and shaped smaller than the hole in plate 54 to fit in the tapered hole within metal plate 54. The round shape was selected to permit waveguide base 63 to seek its own position which is determined, in part, by the surface features of the pole to be tested (e.g. flat spots, indentations, check-edge shapes, etc.) and to insure uniform contact between the pole and elastomeric couplant 65. In turn, then the lower surface of plate 53 is brought into contact with the top surface of plate 54.

Additionally, waveguide base 63 defines two blind cavities therein, one extending into each of the top and bottom surfaces juxtaposed each other with a minimum thickness of material between the blind ends of each of those cavities. The first blind cavity 66 in the lower surface of waveguide base 63, as seen here, is not as deep as elastomeric couplant 65 is thick, and cavity 66 is sized and shaped to constrain an elastomeric couplant 65 to assure uniform contact pressure with the pole by limiting the lateral spread of couplant 65. To provide the most efficient transfer of energy between transducer 35 and the pole, Sorbothane® rubber was selected in the experimentation of the present invention for impedance matching and deformation characteristics that minimize loss of, and variation in, conducted signal levels. Couplant 65 is secured within first blind cavity 66 with a material that permits couplant 65 to deform laterally, and experimentation has shown that a grease couplant or an elastomeric adhesive has been found to be acceptable. The second cavity in the upper surface of waveguide base 63, as seen here, is sized and shaped to receive annulus 75 and is substantially as deep as annulus 75 is thick. In turn, the central hole through annulus 75 (shown dotted in FIG. 8) is sized and shaped to permit shoe 70 of transducer 35 to extend through with annulus 75 forming a collar around shoe 70. It was discovered experimentally that the minimization of the thickness of waveguide base 63 between the two blind cavities minimizes the reflection of higher frequency signals that may enter either of those blind cavities.

At least to other rods 73 and 74 are included as part of the sub-assembly to retain transducer 35 and allow it to float to seek full engagement with the surface of pole 17. At the proximal ends of rods 73 and 74 lock nuts are affixed with springs 76 and 77 mounted around rods 73 and 74 between the lock nuts and the top surface of plate 72. Each of rods 73 and 74 freely pass through holes within plate 72, extend through oversized holes in plate 53 with the distal end of each of rods 73 and 74 being securely fastened to the top surface of waveguide base 63. Thus, when frame 52 is attached to pole 17, the angular relationship of rods 73 and 74 is not fixed with respect to the surface of plate 53 since the oversized holes permit realignment of rods 73 and 74 through plate 53 as waveguide 63 seeks an appropriate orientation in the seat therefore in plate 54.

For best performance, it was found that elastomeric couplant 65 should be larger than shoe 70 of transducer 35, with a 2:1 ratio experimentally found to be acceptable. Further, an elastomeric, or rubber, disk 71 is secured to the other end of transducer 35 to abut against plate 72. Plate 72 is secured to two or more rods 73 and 74, and is compressed against ring 71 and transducer 35 by springs 76 and 77. In this manner, transducer 35 is securely positioned and properly oriented.

As seen here, shoe 70 of transducer 35 extends into annulus 75 and is retained thereby. Then the combination of shoe 70 and annulus 75 is received by the blind cavity in the top of waveguide base 63 with shoe 70 substantially in contact with the blind end of the cavity, and couplant 65 is in contact with the surface of pole 17 with a consistent pressure between them with the bottom surface of plate 54 spaced-apart from the surface of pole 17. When the feet of frame 52 are secured to pole 17, springs 60 and 61 are compressed between frame 52 and plate 53, as illustrated in FIG. 9 to provide adequate coupling pressure between couplant 65 and pole 17, and to permit waveguide base 63 to position itself to provide uniform coupling pressure to the surface of pole 17. Similarly, springs 76 and 77 provide the proper coupling pressure between shoe 70 and waveguide 63. Further, in the mounted configuration the underside of frame 52 is spaced sufficiently far from the surface of pole 17 so that the upper ends of rods 73 and 74 are not interfered with.

FIG. 9 is a schematic view of the coupling assembly 50 of FIG. 8 shown in the compressed state and secured to pole 17. Two or more screws 80 and 81 are used to secure the coupling assembly 50 to pole 17 as shown. When screws 80 and 81 are tightened, springs 60 and 61 are compressed to obtain a pressure level that will minimize variability in coupling as shown by drifting and non-repeatable output signals.

While the attachment assembly, i.e., screws 80 and 81, are used to attach an individual transducer to pole 17, it should be understood that other external attachment assemblies can be used to apply compressive force to the coupling assembly 50. FIGS. 12A and 12B, and 13A and 13B illustrate to other mounting configurations. The first of these, as discussed below, is a mechanical clamping assembly, and the second is strapped configuration.

Figure 12:
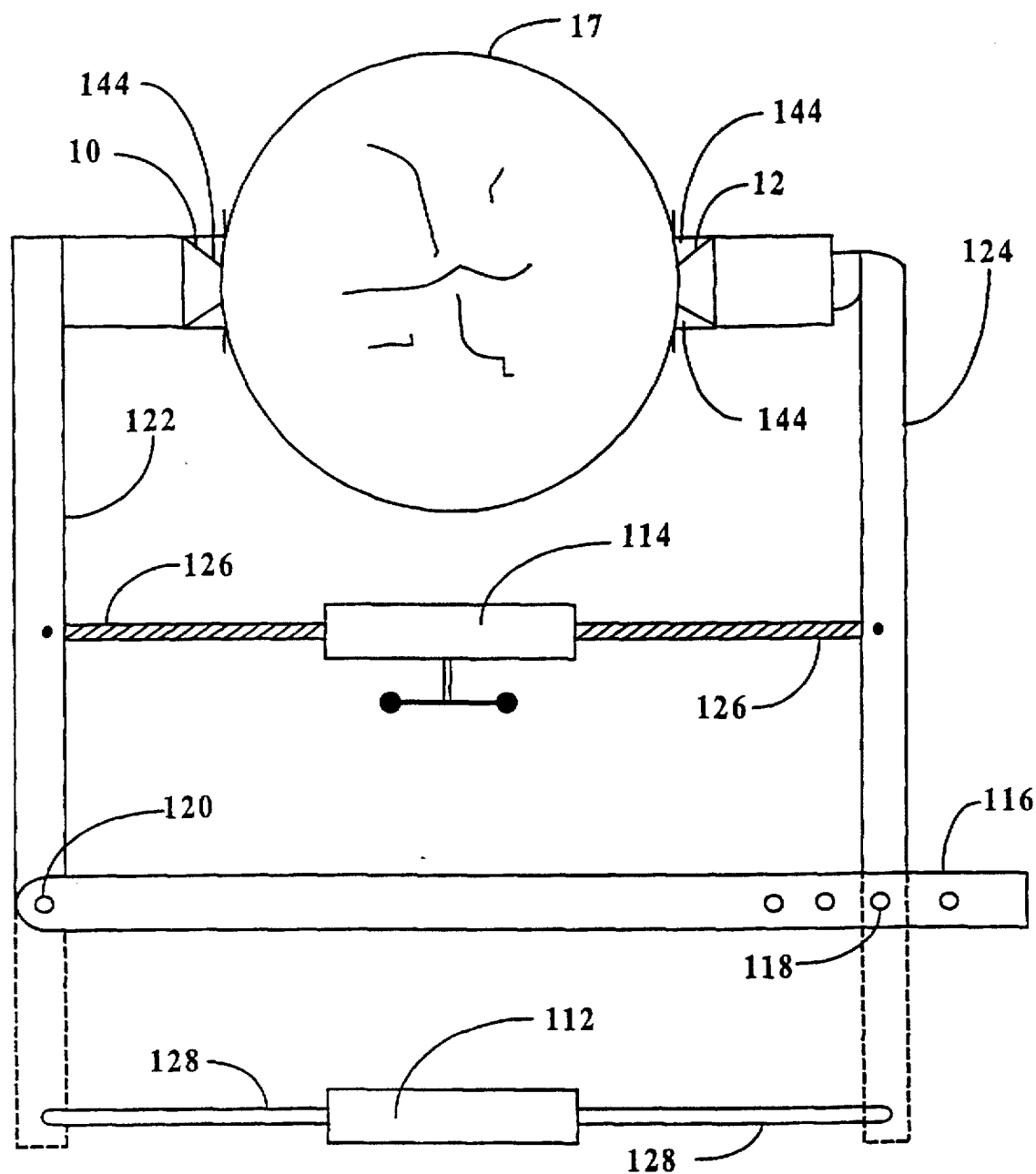
FIGS. 12A and 12B illustrate a second coupling configuration for mounting pulsing and receiving transducers to a pole being tested.
Figure 12B:
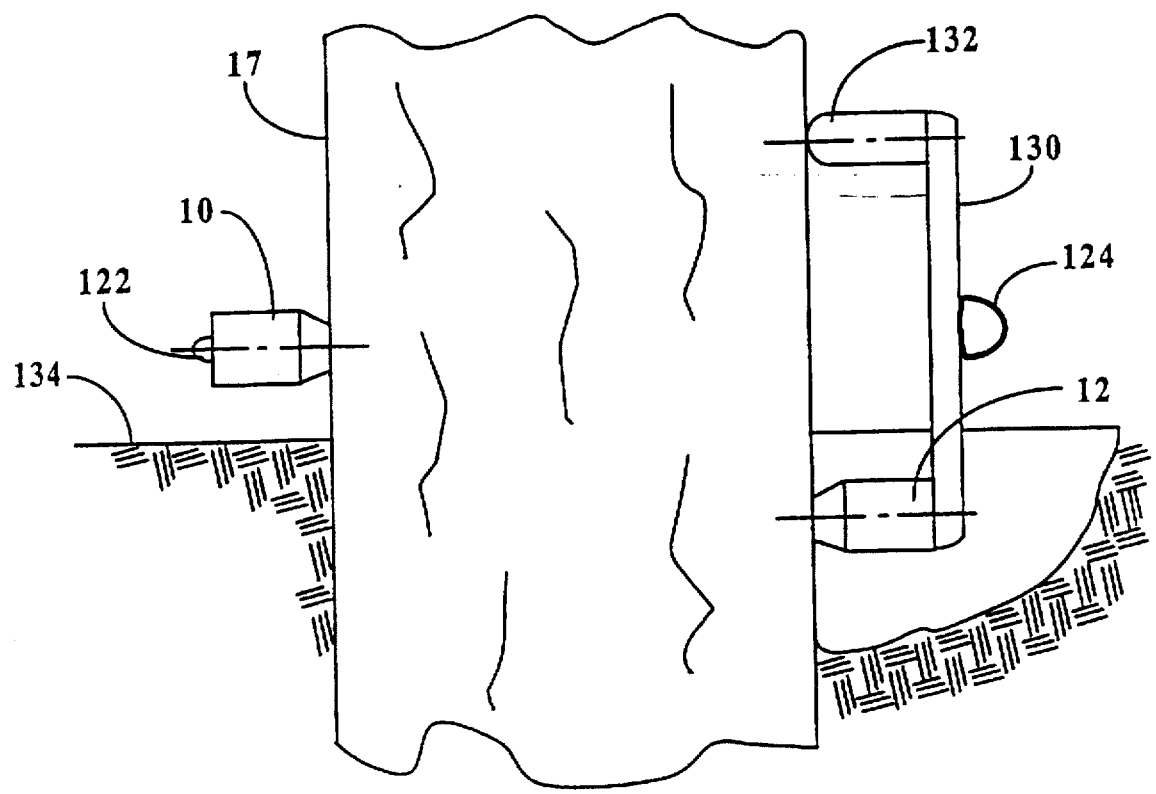

FIGS. 12A and 12B illustrate a caliper type arrangement for mounting pulsing and receiving sub-systems 10 and 12, respectively, in a off-set arrangement on opposite sides of pole 17. FIG. 12A is an end view of pole 17, and FIG. 12B is a side view of pole 17, with the clamping assembly in place in each. Pulsing sub-system 10 is mounted on one end of first arm 122, and receiving sub-system 12 is mounted on one end of second arm 124, and shown being in contact with pole 17. There are three pieces that may be used to interconnect arms 122 and 124, each spaced away from sub-systems 10 and 12, and positioned to not contact pole 17. One is bar 116 that is swivelly mounted to arm 122 at point 120 and arm 124 at point 118. Further bar 116 defines several mounting holes at one end thereof to accommodate different diameter poles 17 by locating an appropriate one of those holes at point 118. An optional second item shown interconnecting arms 122 and 124, is rod 128 and compressive assembly 112 (e.g. mechanical, pneumatic or hydraulic) mounted outside of bar 116 to maintain the ends of arms 122 and 124 at a substantially fixed spacing from each other. An optional third item interconnecting arms 122 and 124 is a tensioning assembly that includes an adjustable mechanical, pneumatic or hydraulic tensioning device 114 and interconnecting cables 126 extending therefrom to each of arms 122 and 124. This tensioning assembly is located between bar 116 and pole 17 when the in place on a pole, and adjustable tensioning device 114 controls the pressure with which each of sub-systems 10 and 12 make with the surface of pole 17. To fully seat pulsing and receiving subsystems 10 and 12 with pole 17, first and second arms 122 and 124 are ideally maintained parallel to each other when in use. In FIG. 12B the offset between sub-systems 10 and 12 is illustrated with sub-system 12 mounted at one end of bridge 130 which in turn is mounted at the end of arm 124. The other end of bridge mates with a spacer 132 which is also in contact with the surface of pole 17. It should be noted here also that FIG. 12B illustrates the mounting of sub-system 12 below the surface 134 in which the pole is standing. Also shown affixed to each of the pulsing and receiving transducers 10 and 12 is a footed bracket 144 to assure consistent pressure between the face of the corresponding transducer and the round wood material to which if is brought into contact.

Figure 13A:
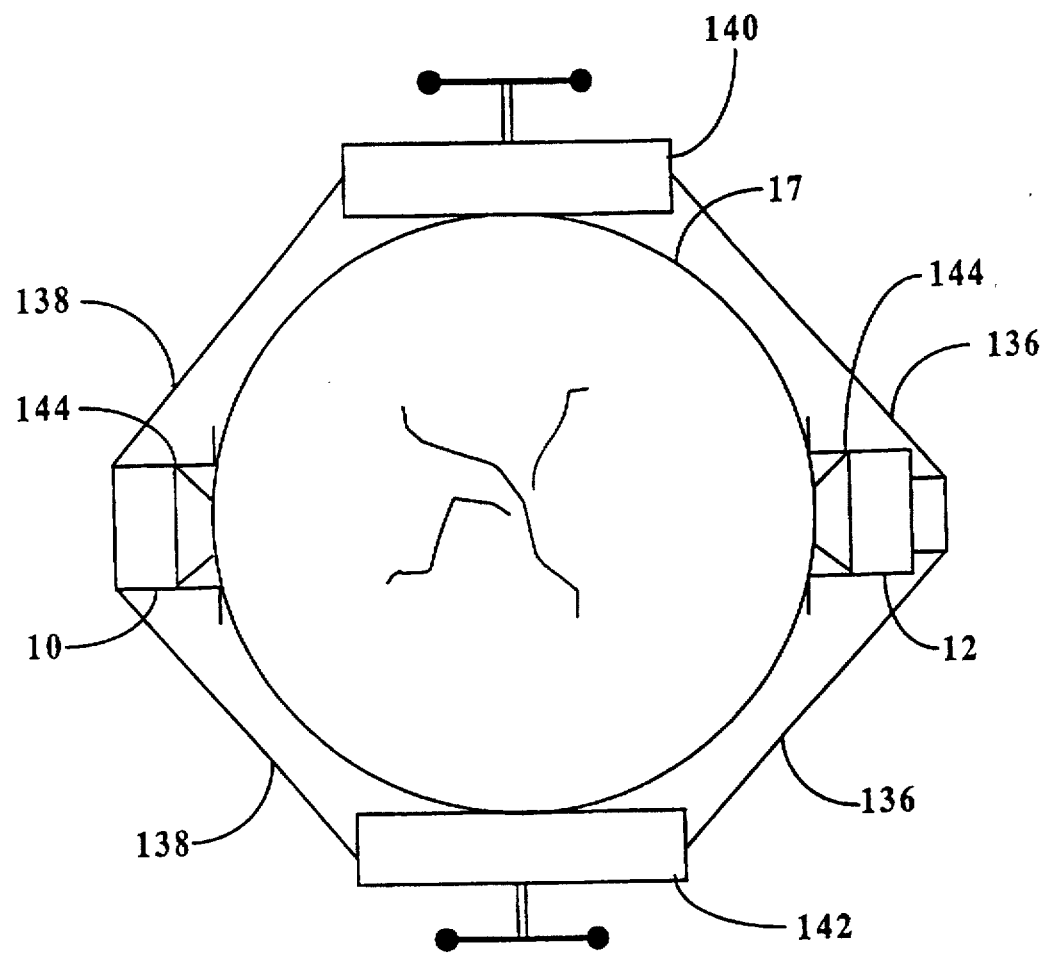
FIGS. 13A and 13B illustrate a third coupling configuration for mounting pulsing and receiving transducers to a pole being tested.
Figure 13B:
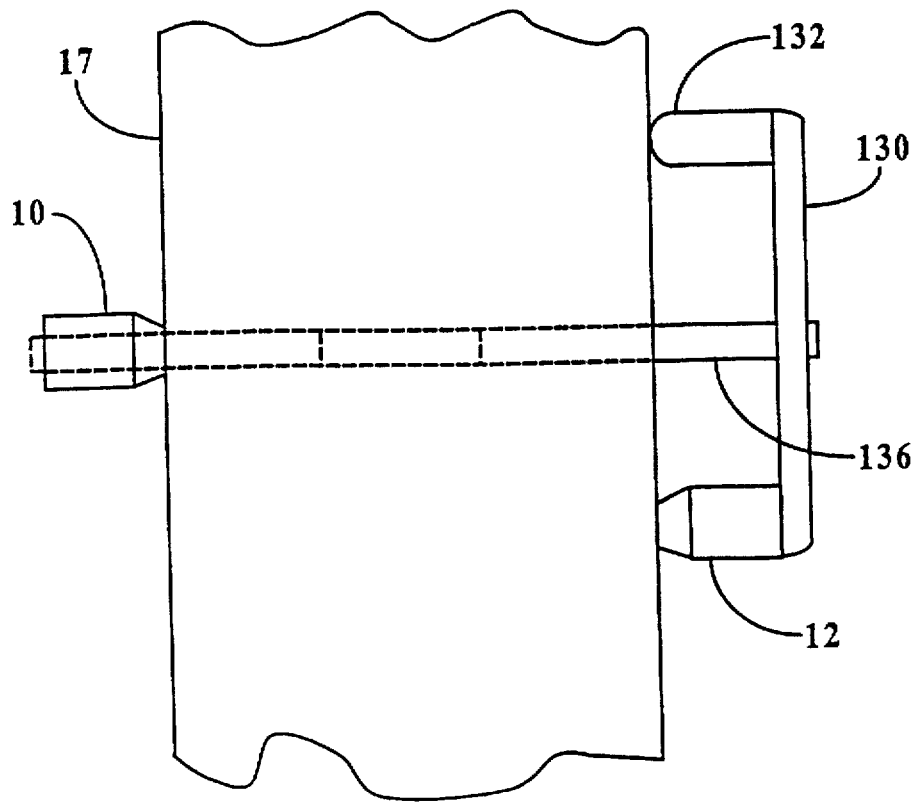

FIGS. 13A and 13B illustrate another mounting system which also has sub-systems 10 and 12 off-set from each other as in the previously discussed mounting system of FIG. 12B. The difference here is that two tensioning straps 136 and 138 and two tensioning devices 140 and 142 maintain sub-systems 10 and 12 in contact with pole 17. Strap 138 extends in either direction from subsystem 10 and coupled with each of tensioning devices 140 and 142, with tensioning devices 140 and 142 also in contact with pole 17 spaced approximately 90° around pole 17 in each direction from sub-system 10. Similarly, strap 136 extends in either direction from bride 130 and coupled with each of tensioning devices 140 and 142, with tensioning devices 140 and 142 on the opposite side from the corresponding ends of strap 138. Tensioning devices 140 and 142 are also spaced approximately 90° around pole 17 in each direction from bridge 130. Also shown affixed to each of the pulsing and receiving transducers 10 and 12 is a footed bracket 144 to assure consistent pressure between the face of the corresponding transducer and the round wood material to which it is brought into contact.

It should further be noted that in each of the illustrative mounting arrangements only two transducer sub-systems where shown mounted to pole 17. Those were offered for illustrative purposes, however, one skilled in the art would easily see how each of those mounting configurations could be expanded to mounted any desired number of transducers to pole 17.

Thus, three attachment assembly configurations have been discussed above and those configurations are by no means exhaustive of all of the ways that attachment might be accomplished, they are representative of the many ways that attachment might be achieved.

Experimental Configurations and Results

In conducting one set of experiments, the following AU system components were used:

| | |
|---|---|
| Amplifier 38: | ATG 301; |
| Preamplifier 37: | Panametrics 5660C; |
| Freq. gen. 33: | Krohnhite 2200; |
| Amplifier 34: | Krohnhite 7500; |
| Pulser (transmitter) 35: | AET AC175L (resonant); |
| and | |
| Receiving transducer 36: | PAC S9208 (broadband). |

In one experiment, frequency generator 33 provided a tone burst output at 60 and 120 kHz. A 175 kHz resonant pulsing transducer was used as pulser 35 because of its high amplitude output over a wide range of tone burst frequencies. A broadband receiving transducer 36 was included to maximize the frequency content of the transmitted signal. Transducers 35 and 36 were mounted in special holders or coupling assemblies (see FIGS. 8 and 9 discussed above) to assure uniform surface contact when clamped. Pressure was controlled pneumatically at 0.5 MPa to minimize the creep of the couplant (Sorbothane® rubber).

Some surface preparation of the test pole was required to remove severely weathered surface material to minimize the energy loss at the interface with the transducers. The received signal was digitized using a DAS 50 A/D converter (Keithley Instruments) 39 at a sampling rate of 1 MHz for a period of 8192 µs. Two hundred waveforms were averaged to minimize the effects of random noise. The waveforms were post-processed in the time and frequency domains using the software package ViewDac (Keithley Instruments) 43 to obtain the AU signal parameter values.

Since most bio-deterioration ultimately leads to cavities in utility poles, this could be approximated and fully controlled by boring holes in the biological center to assess the effect on AU transmission. Three sound Douglas-fir pole specimens of nominal 1.5-m length and 300-mm diameter were used for the experiment. Two of the specimens were low in moisture content of which one was heavily checked from weathering and the other lightly checked; the third specimen was high in moisture content and lightly checked. A hole was bored at the biological center at one end of each of those specimens, hereinafter referred to as the "bored portion"; whereas the other end of each specimen was not altered, thus being referred to hereinafter as the "reference portion". For each of those specimens, three AU readings were made at each of the "bored portions" and the "reference portions".

Following this, the boring of each "bored portion" was sequential increased to 50, 75, and 120 mm diameter along the biological axis of the specimen and three AU readings were taken after each of those sequentially larger borings for each specimen. The AU readings were taken with the pulser 35 placed near the major check 22. Preliminary work had demonstrated that this procedure would minimize energy loss that occurs from transmitting normal to a check (i.e. 90° around the pole from the check instead of adjacent the check). Knots and other visible defects were also avoided in selecting coupling points. Since the arrival time of the waveform was sensitive to both the gain and noise level of the system, a threshold level for arrival was established at 10% above the average background noise.

Ten pole specimens were scanned at about 100 mm intervals along their length with pulser 35 placed adjacent to a major check 22 and moved to alternative sides of check 22, along the length at about 100 mm intervals, pulsing each position at 60 and 120 kHz. Since decay is likely to occur near a major check, the alignment adjacent to the check maximized the probability of decay being in the signal transmission path.

After completing the AU scanning, the specimens were conveyed through an X-ray CT scanner (InVision Technologies CTX5000) to obtain images at 10 mm (nominal) intervals for reference information on growth characteristics and defects. Following this, each specimen was cross-sectioned at the previous AU scanning points to directly evaluate the degree of deterioration. Gross moisture content determinations were also made with a conductance moisture meter to classify the moisture content as "dry" or "wet" (below or above the fiber saturation point).

The objective of these tests was to find a signal parameter, or set of parameters, that could quantify changes in the transmitted signal without being overly sensitive to material variations. It was decided that the ideal signal parameter would be one that shows little sensitivity to material variability between the reference portion and the so called "bored portion" before the bored portion was first bored. Great variability was found between the three measurements in a given region as well as between the reference portion and the unbored "bored portion". Much of this variability was determined to be attributable to checks and growth variations in the poles tested.

Two methods were tried to reduce this variability, including the averaging of the three readings and using the lowest value, with that value appearing to give slightly better results. It is thought that the higher values at the same test point probably resulted from material variability and not the disruption in the path by the hole. Both the shortest transit time and highest frequency centroid parameter values result from the most direct transmission path. Also from these experiments it was discovered that a lower frequency burst rate of 60 kHz resulted in the receipt of an acceptable transmitted signal when the test pole had a high moisture content.

These experiments also revealed that the degree of checking was not a factor in variations of the apparent signal velocity, but the presence of a high moisture content was. An increase in moisture content increases the gross density and decreases the elastic modulus, each of which reduces the velocity in the relationship, $E=\rho v^2$. However, the time centroid parameter showed much more sensitivity to checking than to moisture content. These relationships indicated the need to use multiple signal parameters to minimize extraneous effects on deterioration assessment. By normalizing the data to the reference zone readings, the effect from checking and moisture content was reduced, while maintaining sensitivity to holes, and it was possible to detect a hole at least as small as 50 mm.

Figure 7:
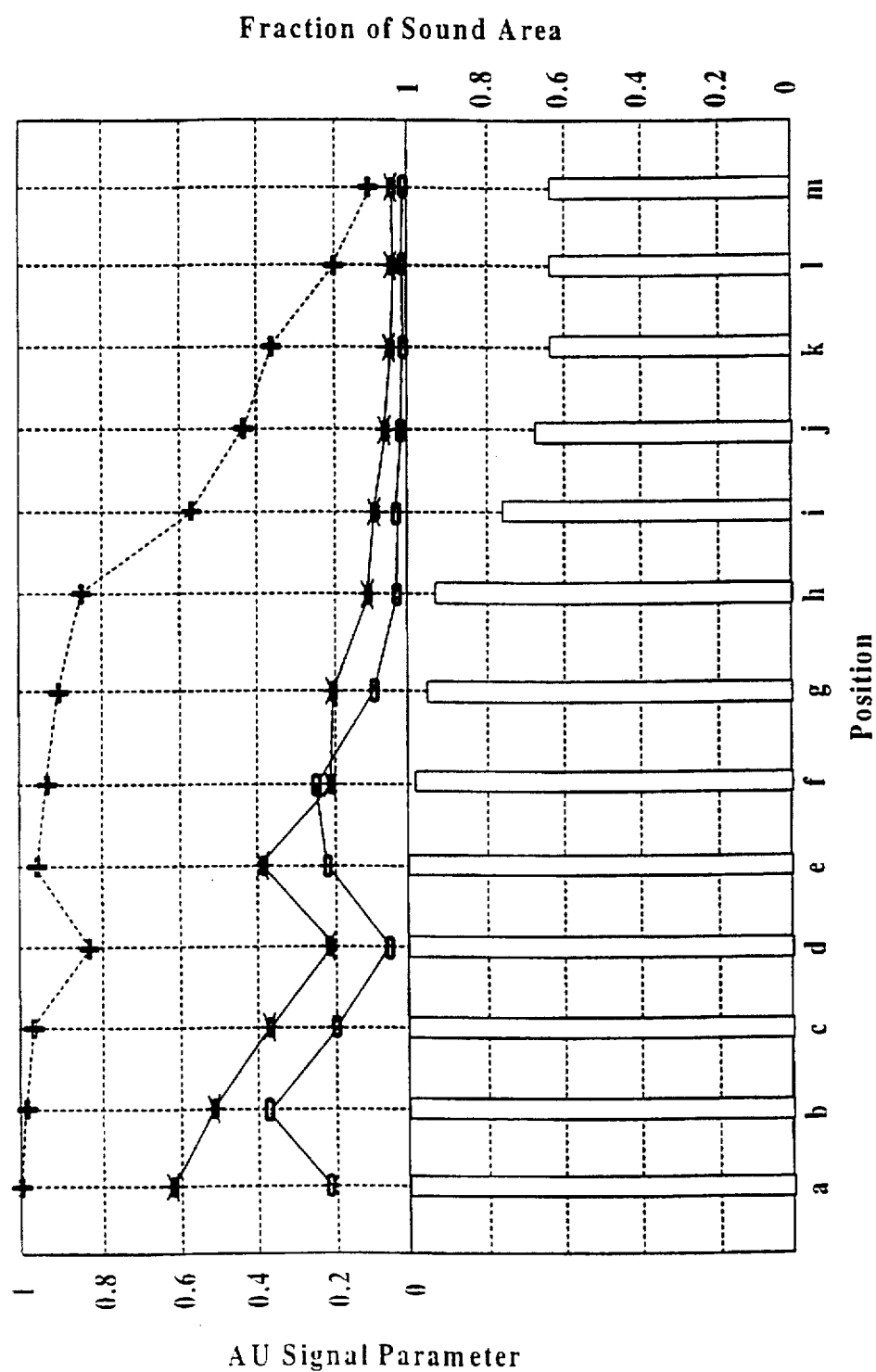
FIG. 7 shows the variation of three signal parameters, namely normalized RMS, normalized velocity and normalized frequency centroid as affected by deterioration in one pole specimen, which has a wide range of decay over the length.

FIG. 7 shows the variation of three signal parameters, namely normalized RMS, normalized velocity and normalized frequency centroid as affected by deterioration in one of the ten deteriorated pole specimens, which had a wide range of decay over the length. The signal parameters were normalized, based on values obtained from a sound specimen. These three parameters are independent, with each having different patterns associated with the degree of deterioration. All three signal parameters were low at position d, which, when cross-sectioned, was found to have checks across the entire diameter of the pole, normal to the transmission direction. However, of the three signal parameters, velocity was least affected, since the small air gap of the check would attenuate the signal, but not substantially affect signal transit time. This variability demonstrates the risk of selecting either an arbitrary signal parameter or a single transmission path for evaluation.

Five major signal parameters: RMS, velocity, centroid time, centroid frequency, and third moment were measured for six selected specimens. These specimens were chosen to be fully representative of the three categories of degradation: namely, non-linear, linearly increasing, and uniform, each defined in relation to the length of the specimen. The two specimens with "uniform degradation" were selected to represent the widest range of signal parameter values of that group of six specimens. A sound specimen was also included for additional data for sound material for comparison with the parameters measured from each of the other specimens.

The data obtained from the tests show that the signal parameter values for RMS, frequency centroid, and third moment are much higher in sound areas than even slightly deteriorated material. This is consistent with previous observations in the literature: R. L. Lemaster and W. W. Wilcox, "The use of acousto-ultrasonics to detect decay in wood-based products", Proceedings, Second International Conference on Acousto-ultrasonics, Atlanta, pp.181–190 (1993); M. Patton-Mallory and R. C. DeGroot, "Detecting brown-rot decay in southern yellow pine by acousto-ultrasonics", Proceedings, Seventh International Nondestructive Testing of Wood Symposium, Pullman, Wash., pp.29–44 (1990); and W. W. Wilcox, "Detection of early stages of wood decay with ultrasonic pulse velocity", Forest Prod. J. 38(5):68–73 (1988).

The abrupt change in these signal parameters infers sensitivity to the presence of incipient decay, which is certain to be at the longitudinal interface of sound wood and advanced decay. From this data, it would not be possible to misclassify a deteriorated area as sound, although there are several instances where the reverse could occur. However, this is clearly a scenario that is acceptable for defining a hazardous condition. At deterioration levels greater than about 5%, only one specimen exceeded a normalized frequency centroid value of about 0.1. However, the RMS value for that specimen was the lowest of all ten specimens.

This specimen was unique in being hollow over much of its length, all others having decay or termite damage had significant residual material remaining. Because of this, a substantial amount of energy was attenuated at the two internal wood-air interfaces in the specimen. Also, transit time increased since the wave would be about six times slower in air than wood.

Two of the signal parameters: velocity and inverse time centroid showed a reasonable degree of increase of the values with increasing sound material. These two signal parameters could be used to assess the degree of deterioration as contrasted with RMS and the frequency-related signal parameters that clearly show either presence or absence of deterioration.

The range of signal parameter values for sound wood was quite variable, particularly for RMS and frequency centroid. That was also the case for the third moment, but the signal values for deteriorated wood were several orders of magnitude lower. Velocity had the most closely-grouped signal values for sound wood, although this may be indicative of an insensitivity to incipient decay that could have affected the other four signal parameters. However, two specimens had velocities for small amounts of deterioration that exceeded those of sound wood.

The following Table II is a look-up table developed from the experimental results for the sensitivity of AU parameters in identifying deterioration and other internal conditions in various Douglas fir and western red cedar specimens, and represents a general trend that uses the five signal parameters discussed above to identify different internal conditions a round wood specimen based on observed experimental results. It is to be expected that the look-up table will vary somewhat for different wood varieties, however no major changes are expected (e.g. there may be a variation in some of the parameter result values that are plus or minus one "x", nothing more substantial than that).

TABLE II

| Inter. Cond. | RMS | Velocity | Centroid time | Centroid freq | Third moment |
|---|---|---|---|---|---|
| CHECKS | xx | 0 | x | x | xx |
| HIGH MOIST C | x | x | 0 | x | x |
| MINOR DECAY | xx | 0 | 0 | xx | xx |
| MAJOR DECAY | xx | xx | xx | xxx | xxx |
| HOLLOW | xxx | xx | x | x | xxx | wherein:
0 no significant change from sound pole value;
x small change from sound pole value;
xx intermediate change from sound pole value;
and
xxx large change from sound pole value.

Thus, from TABLE II it can be seen that each of the various signal parameters vary differently for the various internal conditions that are sought to be determined. RMS is affected most strongly when the pole is hollow; less so when there are internal checks and either major or minor decay; and only slightly when there is a high moisture content. Velocity is only moderately affected by major decay and a hollow spot; slightly by high moisture content; and substantially not at all by checks and minor decay. Centroid time is only affected moderately by major decay; slightly by checks and a hollow spot; and substantially not at all by high moisture content and minor decay. Centroid frequency is affected strongly by major decay; moderately by minor decay; and only slightly by checks, high moisture content and hollow spots. Lastly, Third moment is affected strongly by major decay and hollow spots; moderately by checks and minor decay; and only slightly by high moisture content.

Thus, it can easily be seen that observation of various combinations of two of the parameters can determine the difference between two of the conditions of interest; combinations of three of the parameters enables differentiation between three and in a few combinations perhaps four of the parameters; a combination of four of the parameters improves the determination yet further; and the use of the combination of all five of the parameters assures the ability to distinguish between the five conditions shown here. Stated in a different way, none of the five signal parameters could individually confirm the presence of checks, knots, moisture content, or degrees of decay, reinforcing the need for multi-parameter analysis. It is also of interest that none of the signal parameters were redundant in this classification.

The foregoing techniques were applied to the deteriorated poles. However, with deteriorated poles, there were no clear reference (sound) areas in some of the specimens, necessitating absolute readings. Both bored and deteriorated poles reduced the transmitted signal since the signal path was dependent on reflections from boundaries. In deteriorated portions, the irregularity of the sound/deteriorated interface apparently scattered the signal substantially more than the sound material with bored holes. Another factor reducing reflections was the transition from sound to deteriorated material that provided an acoustical coupling into an area of high attenuation that acted to damp the waves.

A velocity comparison shows an increase in transit time of about 23% from unbored to the 120 mm diameter hole. This hole size, for a 300-mm-diameter specimen, is about 16% of the cross-sectional area. The equivalent reduction in velocity from a similar cross-sectional area of deteriorated material is about 28%, remarkably similar to the result for the holes. Also, a fairly linear relationship of velocity to both hole size and deteriorated area is evident. However, frequency centroid differences show a much more dramatic change for the deteriorated specimens than for those with holes, although the range in the hole fraction was small compared with the deterioration range. In contrast, time centroid appeared more affected by the holes than deterioration, increasing substantially in value for the 50 mm hole. The deteriorated specimens had a more gradual increase in time centroid.

As a result, bored holes of 50 mm or greater are detectible in sound specimens of about 300 mm diameter. This sensitivity requires the use of a "reference" area, giving relative rather than absolute values. Multiple readings are necessary to obtain a signal from the shortest path independent of natural defects. Bio-deterioration in poles can be identified using a number of signal parameters, including RMS, velocity, time centroid, frequency centroid, and third moment, with the most reliable results when using multiple signal parameters. Signal parameters are more sensitive to bio-deterioration than simulated deterioration (bored holes), permitting an absolute determination of both the presence and degree of deterioration.

RMS, frequency centroid, and third moment provide reliable indicators for distinguishing even small amounts of bio-deterioration, but are insensitive to the degree of deterioration. In contrast, velocity and time centroid are reasonably directly related to the degree of deterioration, but are not as sensitive to small levels of deterioration.

Green wood in the form of a standing tree and several green logs shortly after having been cut were also tested using the techniques described above. It was discovered, as might be expected that they responded very similarly to aged poles that did not have an included major check. It was also found that the green wood responded best to simulation with frequencies near the lower end of the frequency spectrum discussed above.

Therefore, given the various testing that was performed and the results obtained, it can easily be seen the present invention extends to all forms of round wood both green and aged independent of the application to which it is used. For example, the present invention extends not only to utility poles, but to poles or columns regardless of their application (e.g. pier pilings, fence posts, structural components, etc.).

The foregoing description of the invention has been presented for purposes of illustration and description. It is not intended to be exhaustive or to limit the invention to the precise forms described, and obviously many other forms are possible in light of the above teaching. The embodiments were chosen in order to explain most clearly the principles of the invention and its practical applications, thereby to enable others in the art to utilize most effectively the invention in various other embodiments and with various other modifications as may be suited to the particular use contemplated. Therefore, the scope of protection for the present invention is not to be limited by the scope of the above discussion, but rather by the scope of the appended claims.

What is claimed is:

1. A caliper assembly disposed to secure components of an acousto-ultrasonics system to a round wood material, said components including a pulsing transducer and a receiving transducer to be secured to said round wood material substantially diametrically opposite to said pulsing transducer along a center line of said round wood material, said caliper assembly comprising:

a first arm having a distal end and a proximal end with said distal end disposed to have affixed thereto said pulsing transducer;

a second arm having a distal end and a proximal end with said distal end disposed to have affixed thereto said receiving transducer;

a pair of rods each having a first end and a second end, each first end of said pair of rods connected to a point between the proximal end and distal end of a different one of said first and second arms;

a spacer bar having a first end and a second end with said first end of said spacer bar swivelly connected to said first arm between the proximal end and distal end of said first arm, and said second end of said spacer bar swivelly connected to said second arm between the proximal end and distal end of said second arm with said spacer bar spaced apart from said pair of rods;

an adjustable assembly having a first end and a second end, each of said first and second ends of said adjustable assembly coupled to a second end of a different one of said pair of rods;

wherein said adjustable assembly is adjustable to maintain the distal ends of each of said first and second arms substantially diametrically opposite each other along the center line of said round wood material to send acousto-ultrasonic waves through the center of said round wood material from said pulsing transducer to said receiving transducer when said caliper assembly is in use.

2. A caliper assembly as in claim 1 further including a pair of footed brackets disposed to be affixed to each of said pulsing and receiving transducers, each of said footed brackets include flanges that extend away from a face of a corresponding one of said pulsing and receiving transducers, said flanges to contact said round wood material to limit compression of the corresponding one of said pulsing and receiving transducers and to assure consistent pressure between each of said pulsing and receiving transducers and said round wood material.

3. A caliper assembly as in claim 1 wherein said adjustable assembly is adjusted to maintain each of said first arm and said second arm substantially parallel to each other when said caliper assembly is in use.

4. A caliper assembly as in claim 1 further includes a bridge of a selected length having a first end and a second end with said bridge connected to the distal end of one of said first arm and said second arm at a point intermediate said first and second ends of said bridge, connected to said first end of said bridge is a corresponding one of said pulsing transducer and said receiving transducer with each transducer having a selected height, and connected to said second end of said bridge is a spacer having a height sufficient to space said bridge away from said round wood material when said caliper assembly is in use.

5. A caliper assembly as in claim 1 wherein said pulsing transducer and said receiving transducer affixed to said distal end of each of said first arm and said second arm, respectfully, make contact with said round wood material when in use, and each of said first and second arms, said pair of rods, said spacer bar and said adjustable assembly are spaced apart from said round wood material when in use.

6. A caliper assembly as in claim 1 wherein each of said first end and second end of said spacer bar is connected to the proximal end of a different one of said first and second arms.

7. A caliper assembly disposed to secure components of an acousto-ultrasonics system to a round wood material, said components including a pulsing transducer and a receiving transducer to be secured to said round wood material substantially diametrically opposite to said pulsing transducer along a center line of said round wood material, said caliper assembly comprising:

- a first arm having a distal end and a proximal end with said distal end disposed to have affixed thereto said pulsing transducer;
- a second arm having a distal end and a proximal end with said distal end disposed to have affixed thereto said receiving transducer;
- a spacer bar having a first end and a second end with said first end of said spacer bar swivelly connected to said first arm between the proximal end and the distal end of said first arm, and said second end of said spacer bar swivelly connected to said second arm between the proximal end and the distal end of said second arm;
- a pair of cables, each of said cables having a first end and a second end with said first end of each cable of said pair of cables connected to a different one of said first and second arms between said proximal end and said distal end of the corresponding one of said first and second arms with said pair of cables spaced apart from said spacer bar;
- an adjustable cable tensioning device coupled to the second end of each of said pair of cables, and said adjustable cable tensioning device to maintain the distal ends of each of said first and second arms substantially diametrically opposite each other diametrically along the center line of said round wood material to send acousto-ultrasonic waves through the center of said round wood material from said pulsing transducer to said receiving transducer when said caliper assembly is in use.

8. A caliper assembly as in claim 7 wherein each of said first end and second end of said spacer bar is connected to the proximal end of a different one of said first and second arms.

9. A caliper assembly as in claim 7 further including a pair of footed brackets disposed to be affixed to each of said pulsing and receiving transducers, each of said footed brackets include flanges that extend away from a face of a corresponding one of said pulsing and receiving transducers, said flanges to contact said round wood material to limit compression of the corresponding one of said pulsing and receiving transducers and to assure consistent pressure between each of said pulsing and receiving transducers and to assure consistent pressure between each of said pulsing and receiving transducers and said round wood material.

10. A caliper assembly as in claim 7 wherein said adjustable cable tensioning device is adjusted to maintain each of said first arm and said second arm substantially parallel to each other when said caliper assembly is in use.

11. A caliper assembly as in claim 7 further includes a bridge of a selected length having a first end and a second end with said bridge connected to the distal end of one of said first arm and said second arm at a point intermediate said first and second ends of said bridge, connected to said first end of said bridge is a corresponding one of said pulsing transducer and said receiving transducer with each transducer having a selected height, and connected to said second end of said bridge is a spacer having a height sufficient to space said bridge away from said round wood material when said caliper assembly is in use.

12. A caliper assembly as in claim 7 wherein said pulsing transducer and said receiving transducer affixed to said distal end of each of said first arm and said second arm, respectfully, make contact with said round wood material when in use, and each of said first and second arms, said pair of cables, said spacer bar and said adjustable cable tensioning device are spaced apart from said round wood material when in use.

13. A caliper assembly disposed to secure components of an acousto-ultrasonics system to a round wood material, said components including a pulsing transducer and a receiving transducer to be secured to said round wood material substantially diametrically opposite to said pulsing transducer along a center line of said round wood material, said caliper assembly comprising:

- a first arm having a distal end and a proximal end with said distal end disposed to have affixed thereto said pulsing transducer;
- a second arm having a distal end and a proximal end with said distal end disposed to have affixed thereto said receiving transducer;
- a spacer bar having a first end and a second end with said first end of said spacer bar swivelly connected to said first arm between the proximal end and the distal end of said first arm, and said second end of said spacer bar swivelly connected to said second arm between the proximal end and the distal end of said second arm;
- a pair of cables, each of said cables having a first end and a second end with said first end of each cable of said pair of cables connected to the proximal end of a different one of said first and second arms with said pair of cables spaced apart from said spacer bar;
- an adjustable cable tensioning device coupled to the second end of each of said pair of cables, and said adjustable cable tensioning device to maintain the distal ends of each of said first and second arms substantially diametrically opposite each other diametrically along the center line of said round wood material to send acousto-ultrasonic waves through the center of said round wood material from said pulsing transducer to said receiving transducer when said caliper assembly is in use.

14. A caliper assembly disposed to secure components of an acousto-ultrasonics system to a round wood material, said components including a pulsing transducer and a receiving transducer to be secured to said round wood material substantially diametrically opposite to said pulsing transducer along a center line of said round wood material, said caliper assembly comprising:

- a first arm having a distal end and a proximal end with said distal end disposed to have affixed thereto said pulsing transducer;
- a second arm having a distal end and a proximal end with said distal end disposed to have affixed thereto said receiving transducer;
- a pair of rods each having a first end and a second end, each first end of said pair of rods connected to the proximal end of a different one of said first and second arms;
- a spacer bar having a first end and a second end with said first end of said spacer bar swivelly connected to said first arm between the proximal end and distal end of said first arm, and said second end of said spacer bar swivelly connected to said second arm between the proximal end and distal end of said second arm with said spacer bar spaced apart from said pair of rods;

an adjustable assembly having a first end and a second end, each of said first and second ends of said adjustable assembly coupled to a second end of a different one of said pair of rods;

wherein said adjustable assembly is adjustable to maintain the distal ends of each of said first and second arms substantially diametrically opposite each other along the center line of said round wood material to send acousto-ultrasonic waves through the center of said round wood material from said pulsing transducer to said receiving transducer when said caliper assembly is in use.

* * * * *